(12) United States Patent
Ichim

(10) Patent No.: US 10,532,128 B2
(45) Date of Patent: Jan. 14, 2020

(54) IMPLANTABLE CELLULAR THERAPY DEVICE FOR TREATMENT OF GRAFT VERSUS HOST DISEASE AND TOLERANCE INDUCTION

(71) Applicant: Viera Bioscience, Inc., Rancho Santa Fe, CA (US)

(72) Inventor: Thomas Ichim, San Diego, CA (US)

(73) Assignee: VIERA BIOSCIENCE, INC., Rancho Santa Fe, CA (US)

(*) Notice: Subject to any disclaimer, the term of this patent is extended or adjusted under 35 U.S.C. 154(b) by 0 days.

(21) Appl. No.: 15/353,600

(22) Filed: Nov. 16, 2016

(65) Prior Publication Data

US 2017/0136153 A1 May 18, 2017

Related U.S. Application Data

(60) Provisional application No. 62/256,919, filed on Nov. 18, 2015.

(51) Int. Cl.
*A61L 27/56* (2006.01)
*A61L 27/38* (2006.01)
*C12N 5/00* (2006.01)
*A61M 5/142* (2006.01)

(52) U.S. Cl.
CPC ....... *A61L 27/3834* (2013.01); *A61L 27/3895* (2013.01); *A61L 27/56* (2013.01); *C12N 5/0068* (2013.01); *A61L 2300/414* (2013.01); *A61L 2300/426* (2013.01); *A61M 5/14276* (2013.01); *A61M 2202/09* (2013.01); *A61M 2202/097* (2013.01)

(58) Field of Classification Search
None
See application file for complete search history.

(56) References Cited

U.S. PATENT DOCUMENTS

| | | | |
|---|---|---|---|
| 5,372,581 A | 12/1994 | Anderson | |
| 5,415,665 A | 5/1995 | Hessel | |
| 5,725,854 A | 3/1998 | Selawry | |
| 5,759,534 A | 6/1998 | Selawry | |
| 5,843,430 A | 12/1998 | Selawry | |
| 5,849,285 A | 12/1998 | Selawry | |
| 5,958,404 A | 9/1999 | Selawry | |
| 6,149,907 A | 11/2000 | Selawry | |
| 7,147,626 B2 | 12/2006 | Goodman | |
| 7,955,288 B2 * | 6/2011 | Hansen | A61B 10/0291 604/1 |
| 8,883,210 B1 * | 11/2014 | Truncale | C12N 5/0654 424/484 |
| 2010/0178700 A1 * | 7/2010 | Fletcher | A61K 35/26 435/377 |

FOREIGN PATENT DOCUMENTS

CA 2453198 1/2004

OTHER PUBLICATIONS

Flynn et al. "Proliferation and differentiation of adipose-derived stem cells on naturally derived scaffolds". Biomaterials. 2008, 29, pp. 1862-1871.*
Eshel et al. "Analysis of thymic stromal cell subpopulations grown in vitro on extracellular matrix in defined medium". The Journal of Immunology. 1990, vol. 144, No. 5, pp. 1554-1562.*
Orlic, D., et al., Bone marrow cells regenerate infarcted myocardium. Nature, 2001, 410(6829): p. 701-5.
Hamano, K., et al., Local implantation of autologous bone marrow cells for therapeutic angiogenesis in patients with ischemic heart disease: clinical trial and preliminary results. Jpn Circ J, 2001. 65(9): p. 845-7.
Stamm, C., et al., Autologous bone-marrow stem-cell transplantation for myocardial regeneration. Lancet, 2003, 361(9351): p. 45-6.
Kondziolka, D., et al., Neurotransplantation for patients with subcortical motor stroke: a phase 2 randomized trial. J Neurosurg, 2005. 103(1): p. 38-45.
Kordella, T., The Edmonton Protocol. The future of islet transplantation? Diabetes Forecast, 2003, 56(2): p. 58-62.
Shapiro, AM., et al., International trial of the Edmonton protocol for islet transplantation. N Engl J Med, 2006. 355(13): p. 1318-30.
Bang, O.Y., et al., Autologous mesenchymal stem cell transplantation in stroke patients. Ann Neurol, 2005. 57(6): p. 874-82.
Mohamadnejad, M., et al., Phase I human trial of autologous bone marrowhematopoietic stem cell transplantation in patients with decompensated cirrhosis. World J Gastroenterol, 2007. 13(24): p. 3359-63.
Wang, X.X., et al., Transplantation of autologous endothelial progenitor cells may be beneficial in patients with idiopathic pulmonary arterial hypertension: a pilot randomized controlled trial. J Am Coll Cardiol, 2007. 49(14): p. 1566-71.
Nizankowski, R., et al., The treatment of advanced chronic lower limb ischaemia with marrow stem cell autotransplantation. Kardiol Pol, 2005, 63(4): p. 351-60; discussion 361.

(Continued)

*Primary Examiner* — Vera Afremova
(74) *Attorney, Agent, or Firm* — Knobbe, Martens, Olson & Bear LLP

(57) ABSTRACT

Implantable devices comprising a scaffold, cells, and/or therapeutic molecules are provided. Uses include inhibition of pathological immunity, elaboration of therapeutic growth factors, and immune augmentation. The implantable device may contain a porous substrate structure to which therapeutic cells are adherent, which can be implanted and explanted from a patient. In another embodiment, a medical device includes a porous substrate seeded with therapeutic cells, said device comprising of an additional layer allowing free exchange of molecules without cell escape. Said medical device is seeded with thymic medullary epithelial cells or progenitors of said thymic medullary epithelial cells. In conditions where tolerance to alloreactive donor cells is desired, the thymic medullary epithelial cells or progenitors thereof are derived from recipient cells. In conditions where tolerance to alloreactive recipient cells is desired, the thymic medullary epithelial cells or progenitors thereof are derived from donor cells.

15 Claims, No Drawings

(56) References Cited

OTHER PUBLICATIONS

Kim, S.Y., et al., Siberian Sturgeon Oocyte Extract Induces Epigenetic Modifications of Porcine Somatic Cells and Improves Developmental Competence of SCNT Embryos. Asian-Australas J Anim Sci, 2014. 27(2): p. 266-77.

Wen, D., et al., Histone variant H3.3 is an essential maternal factor for oocyte reprogramming. Proc Natl Acad Sci USA, 2014, 111(20): p. 7325-30.

Preskey, D., et al., Synthetically modified mRNAfor efficient and fast human iPS cell generation and direct transdif.ferentiation to myoblasts. Biochem Biophys Res Commun, 2015.

Mesquita, F.C., et al., Generation of human iPS cell line ihFib3.2 from dermal fibroblasts. Stem Cell Res, 2015. 15(3): p. 445-448.

Hamalainen, R.H. and A Suomalainen, Generation and Characterization of Induced Pluripotent Stem Cells from Patients with mtDNA Mutations. Methods Mol Biol, 2016. 1353: p. 65-75.

Thery, C., M. Ostrowski, and E. Segura, Membrane vesicles as conveyors of immune responses. Nature reviews. Immunology, 2009. 9(8): p. 581-93.

Ludwig, AK. and B. Giebel, Exosomes: Small vesicles participating in intercellular communication. The international journal of biochemistry & cell biology, 2011.

Alvarez-Erviti, L., et al., Lysosomal dysfunction increases exosome-mediated alphasynuclein release and transmission. Neurobiology of disease, 2011, 42(3): p. 3 60-7.

Silverman, J.M. and N.E. Reiner, Exosomes and other microvesicles in infection biology: organelles with unanticipated phenotypes. Cellular microbiology, 2011. 13(1): p. 1-9.

Pan, B. T. and RM. Johnstone, Fate of the transferrin receptor during maturation of sheep reticulocytes in vitro: selective externalization of the receptor. Cell, 1983. 33(3): p. 967-78.

Alonso, R., et al., Diacylglycerol kinase alpha regulates the formation and polarisation of mature multivesicular bodies involved in the secretion of Fas ligandcontaining exosomes in T lymphocytes. Cell death and differentiation, 2011. 16(7): p. 1161-73.

Zhang, H., et al., CD4(+) T cell-released exosomes inhibit CD8(+) cytotoxic Tlymphocyte responses and antitumor immunity. Cellular & molecular immunology, 2011. 8(1): p. 23-30.

Mathews, J.A., et al., CD23 Sheddase A disintegrin and metal-loproteinase JO (ADAMJO) is also required for CD23 sorting into B cell-derived exosomes. The Journal ofbioiogical chemistry, 2010. 285(48): p. 37531-41.

Buschow, S.I., et al., MHC class II-associated proteins in B-cell exosomes and potential functional implications for exosome biogenesis. Immunology and cell biology, 2010. 88(8): p. 851-6.

Hwang, I. and D. Ki, Receptor-mediated T cell absorption of antigen presenting cellderived molecules. Frontiers in bioscience : a journal and virtual library, 2011. 16: p. 411-21.

Viaud, S., et al., Updated technology to produce highly immunogenic dendritic cellderived exosomes of clinical grade: a critical role of interferon-gamma. Journal of immunotherapy, 2011. 34(1): p. 65-75.

Clayton, A, et al., Cancer exosomes express CD39 and CD73, which suppress T cells through adenosine production. Journal of immunology, 2011. 187(2): p. 676-83.

Battke, C., et al., Tumour exosomes inhibit binding of tumour-reactive antibodies to tumour cells and reduce ADCC. Cancer immunology, immunotherapy : CII, 2011. 60(5): p. 639-48.

Lachenal, G., et al., Release of exosomes from differentiated neurons and its regulation by synaptic glutamatergic activity. Molecular and cellular neurosciences, 2011, 46(2): p. 409-18.

Faure, J., et al., Exosomes are released by cultured cortical neurones. Molecular and cellular neurosciences, 2006. 31( 4): p. 642-8.

Fitzner, D., et al., Selective transfer of exosomes from oligodendrocytes to microglia by macropinocytosis. Journal of cell science, 2011. 124(Pt 3): p. 447-58.

Mincheva-Nilsson, L. and V. Baranov, The role of placental exosomes in reproduction. American journal ofreproductive immunology, 2010, 63(6): p. 520-33.

Mincheva-Nilsson, L., et al., Placenta-derived soluble MHC class I chain-related molecules down-regulate NKG2D receptor on peripheral blood mononuclear cells during human pregnancy: a possible novel immune escape mechanism for fetal survival, Journal of immunology, 2006. 176(6): p. 3565-92.

Murphy, M.P., et al., Allogeneic endometrial regenerative cells: an "Off the shelf solution" for critical limb ischemia? Journal of translational medicine, 2008. 6: p. 45.

Raposo, G., et al., B lymphocytes secrete antigen-presenting vesicles. The Journal of experimental medicine, 1996. 183(3): p. 1161-72.

Abusamra, A.J., et al., Tumor exosomes expressing Fas ligand mediate CD8+ T-cell apoptosis. Blood cells, molecules & diseases, 2005. 35(2): p. 169-73.

Ichim, T.E., R. Zhong, and W.P. Min, Prevention of allograft rejection by in vitro generated tolerogenic dendritic cells. Transplant immunology, 2003, 11(3-4): p. 295-306.

Popov, I., et al., Preventing autoimmune arthritis using antigen-specific immature dendritic cells: a novel tolerogenic vaccine. Arthritis research & therapy, 2006, 8(5): p. RI41.

Luketic, L., et al., Antigen presentation by exosomes released from peptide-pulsed dendritic cells is not suppressed by the presence of active CTL. Journal of immunology, 2007. 179(8): p. 5024-32.

Segura, E., S. Amigorena, and C. Thery, Mature dendritic cells secrete exosomes with strong ability to induce antigen-specific effector immune responses. Blood cells, molecules & diseases, 2005. 35(2): p. 89-93.

Ruffner, M.A., et al., B7-J/2, but not PD-LI/2 molecules, are required on IL-10-treated tolerogenic DC and DC-derived exosomes for in vivo function. European journal of immunology, 2009. 39(11): p. 3084-90.

Yang, X., et al., Exosomes derived from immature bone marrow dendritic cells induce tolerogenicity of intestinal transplantation in rats. The Journal of surgical research, 2011. 171(2): p. 826-32.

Peche, H., et al., Induction of tolerance by exosomes and short-term immunosuppression in a fully MHC-mismatched rat cardiac allograft model. American journal of transplantation : official journal of the American Society of Transplantation and the American Society of Transplant Surgeons, 2006. 6(7): p. 1541-50.

Kim, S.H., et al., MHC class 11+ exosomes in plasma suppress inflammation in an antigen-specific and Fas ligand/Fas-dependent manner. Journal of immunology, 2007. 179(4): p. 2235-41.

Marleau, AM., et al., Chimerism of murine fetal bone marrow by maternal cells occurs in late gestation and persists into adulthood Laboratory investigation; a journal of technical methods and pathology, 2003. 83(5): p. 673-81.

Kara. R.J., et al., Fetal Cells Traffic to Injured Maternal Myocardium and Undergo Cardiac Differentiation. Circulation research, 2011.

Khashan, AS., et al., Pregnancy and the risk of autoimmune disease, PloS one, 2011. 6(5): p. eI9658.

Emerudh, J., G. Berg, and J. Mjosberg; Regulatory T helper cells in pregnancy and their roles in systemic versus local immune tolerance. American journal of reproductive immunology; 2011. 66 Suppl 1: p. 31-43.

Lin, Q.D. and L.H. Qiu, Pathogenesis, diagnosis, and treatment of recurrent spontaneous abortion with immune type. Frontiers of medicine in China, 2010. 4(3): p. 275-9.

Pandey, M.K., R. Rani, and S. Agrawal, An update in recurrent spontaneous abortion. Archives of gynecology and obstetrics, 2005. 272(2): p. 95-108.

Frangsmyr, L., et al., Cytoplasmic microvesicular form of Fas ligand in human early placenta: switching the tissue immune privilege hypothesis from cellular to vesicular level. Molecular human reproduction, 2005. 11(1): p. 35-41.

Taylor, D.D., S. Akyol, and C. Gercel-Taylor, Pregnancy-associated exosomes and their modulation of T cell signaling. Journal of immunology, 2006. 176(3): p. 1534-42.

Sabapatha, A, C. Gercel-Taylor, and D.D. Taylor, Specific isolation of placenta derived exosomes from the circulation of pregnant

(56) References Cited

OTHER PUBLICATIONS women and their immunoregulatory consequences. American journal of reproductive immunology; 2006, 56(5-6): p. 345-55.

Hedlund, M., et al., Human placenta expresses and secretes NKG2D ligands via exosomes that down-modulate the cognate receptor expression: evidence for immunosuppressivefunction. Journal of immunology, 2009. 183(1): p. 340-51.

Forger, F., et al., Pregnancy induces numerical and functional changes of CD4+CD25 high regulatory T cells in patients with rheumatoid arthritis. Annals of the rheumatic diseases, 2008. 67(7): p. 984-90.

Airas, L.; et al., Immunoregulatory factors in multiple sclerosis patients during and after pregnancy: relevance of natural killer cells. Clinical and experimental immunology, 2008. 151(2): p. 235-43.

Gatson; N.N.; et al., Induction of pregnancy during established EAE halts progression of CNS autoimmune injury via pregnancy-specific serum factors. Journal of neuroimmunology, 2011. 230(1-2): p. 105-13.

Taylor, D.D. and C. Gercel-Taylor, Tumour-derived exosomes and their role in cancer-associated T-cell signalling defects. British journal of cancer, 2005. 92(2): p. 305-11.

Valenti, R., et al., Tumor-released microvesicles as vehicles of immunosuppression. Cancer research, 2007. 67(7): p. 2912-5.

Greten, T.F., M.P. Manns, and F. Korangy, Myeloid derived suppressor cells in human diseases. International immunopharmacology, 2011. 11 (7): p. 802-7.

Szajnik, M., et al., Tumor-derived microvesicles induce, expand and up-regulate biological activities of human regulatory T cells (Treg), PloS one, 2010. 5(7): p. eII469.

Weiner, H.L., et al., Oral tolerance. Immunological reviews, 2011. 241(1): p. 241-59.

Wei, W., et al., A multicenter, double-blind, randomized, controlled phase III clinical trial of chicken type II collagen in rheumatoid arthritis. Arthritis research & therapy, 2009. 11(6): p. RI80.

Benson, J.M., et al., Oral administration of myeiin basic protein is superior to myelin in suppressing established relapsing experimental autoimmune encephalomyelitis, Journal of immunology, 1999. 162(10): p. 6247-54.

Hafter, D.A., et al., Oral administration of myelin induces antigen-specific TGF-beta I secreting T cells in patients with multiple sclerosis. Annals of the New York Academy of Sciences, 1997. 835: p. 120-31.

Ostman, S., M. Taube, and E. Telemo, Tolerosome-induced oral tolerance is MHC dependent. Immunology, 2005. 116( 4): p. 464-76.

Almqvist, N., et al., Serum-derived exosomes from antigen-fed mice prevent allergic sensitization in a model of allergic asthma. Immunology, 2008. 125( 1): p. 21-7.

Meng, X., et al., Endometrial regenerative cells: a novel stem cell population. Journal of translational medicine, 2007, 5: p. 57.

Ichim, T,E., et al., Placental mesenchymal and cord blood stem cell therapy for dilated cardiomyopathy. Reproductive biomedicine online, 2008. 16(6): p. 898-905.

Ichim, T.E., et al., Feasibility of combination allogeneic stem cell therapy for spinal cord injury: a case report. International archives of medicine, 2010. 3: p. 30.

Yang, W.Z., et al., Human umbilical cord blood-derived mononuclear cell transplantation: case series of 30 subjects with hereditary ataxia. Journal of translational medicine, 2011. 9: p. 65.

\* cited by examiner

IMPLANTABLE CELLULAR THERAPY DEVICE FOR TREATMENT OF GRAFT VERSUS HOST DISEASE AND TOLERANCE INDUCTION

CROSS-REFERENCE TO RELATED APPLICATIONS

The present application claims the benefit of priority to U.S. Provisional Patent Application No. 62/256,919, filed Nov. 18, 2015, the disclosure of which is incorporated by reference herein in its entirety.

FIELD

The disclosure pertains to the area of medical devices, particularly the disclosure pertains to implantable devices containing living cells, said living cells endowing various therapeutic properties to recipient of cell implantable device.

BACKGROUND

The basic concept of cellular therapy has been known since the time of Paracelsus, who in the 16$^{th}$ Century stated "Heart heals the heart, lung heals lung, spleen heals spleen; like cures like." These philosophical ponderings of this alchemist were reduced to practice by the controversial Swiss physician Paul Niehans who utilized fetal xenogeneic cells to treat a variety of ailments in the early part of the last century. In recent times cell therapy has been gaining momentum for treatment of a wide variety of disorders. By far the most widely established use of cell therapy is for treatment of leukemias in the form of bone marrow transplantation.

The first hematopoietic stem cell transplant, or bone marrow transplant, was performed in 1956 by Dr. E. Donnall Thomas using bone marrow cells isolated from an identical twin donor for a recipient who had leukemia. The idea was that if the patient was irradiated with high doses, then the radiation would kill all of the leukemia cells. Unfortunately, the radiation would also destroy the healthy bone marrow stem cells. So the idea was to utilize donor bone marrow to replenish the recipient with healthy hematopoietic stem cells. Dr. Thomas, along with Joseph E. Murray, won the Nobel Prize in 1990 for this discovery.

As described above, transfer of bone marrow stem cells has been performed for decades. Scientists have wondered if the bone marrow stem cell possesses the potential to differentiate into all the different types of blood cells, maybe it can also differentiate into other cells as well. This process was originally termed "transdifferentiation". The first report of transdifferentiation to appear in the major medical literature was a paper by Orlic et al. [1], in which mouse bone marrow derived stem cells were injected into mice that were given an experimental heart attack. The interesting thing about this experiment was that the bone marrow stem cells used were labeled to glow green. The donor animals were genetically engineered to express the green fluorescent protein (GFP) gene throughout their bodies. This essentially means that all cells derived from the GFP donor mice were green. Additionally, the experimenters purified the mouse equivalent of the human CD34 bone marrow hematopoietic stem cell. The molecular markers used where positivity for stem cell antigen (SCA-1) and negativity for the lineage markers (lin negative). Following induction of a heart attack by ligation of one of the coronary arteries, the researchers implanted the cells in the area of infarct. The mice which received implanted hematopoietic stem cells, but not control cells, had increased pumping ability of the heart and decreased levels of heart damage.

Numerous other experiments have demonstrated efficacy of cell therapy in animals and humans for non-hematopoietic purposes. For example Japanese researchers have demonstrated that when bone marrow cells are injected into the heart muscle of patients undergoing bypass surgery a therapeutic effect is observed. The idea was that the injected bone marrow cells will stimulate production of new blood vessels and thereby increase oxygenation to the heart [2]. The procedure, although highly invasive, was associated with no treatment related adverse effects and 3 out of the 5 patients had increased blood vessel production as assessed radiologically, as well as improved cardiac function. This first demonstration in 2001, was repeated by numerous investigators. In 2003, the study was repeated using CD133 purified bone marrow stem cells and published in the prestigious journal Lancet [3], reporting positive results. Subsequently numerous studies have been conducted in the area of cardiology demonstrating that administration of a patient's own bone marrow is associated with positive outcome. Another example of cell therapy was a program conducted by Layton Biosciences, who developed a homogeneous cellular population by differentiating a proprietary teratocarcinoma cell line into neurons using a retinoic acid based protocol. These cells, called LBS-neurons were utilized in several clinical trials. In one trial surgical implantation of these cells was demonstrated to induce improvement based on the functional ESS score in some patients [4].

Cell therapy has also been used in the treatment of diabetes, for example, the Edmonton Protocol involves intrahepatic administration of donor islets under the cover of calcineurin-sparing immune suppressants. This approach has resulted in reduced insulin requirements of Type I diabetics, and in some cases achievement of complete insulin independence [5, 6]. Other uses of cell therapy include treatment of stroke [7], liver failure [8], lung failure [9], and peripheral artery disease [10].

The use of cell therapy for immune modulation has been conducted primarily in terms of immune stimulation, as is the case of Provenge, the FDA approved therapeutic vaccine for prostate cancer. Unfortunately, the use of cell therapy for tolerance induction has not been performed in an applicable manner that is commercially relevant.

SUMMARY

It is therefore an aspect of this disclosure to provide improved cell therapies for immune modulation. It is a related aspect to provide implantable devices for inhibition of pathological immunity, elaboration of therapeutic growth factors, and immune augmentation.

Some embodiments disclosed herein relate to an implantable device. In some embodiments, the implantable device includes a therapeutic cell population, a matrix capable of maintaining viability and function of said therapeutic cell population, and a layer of material with selective permeability surrounding said matrix capable of maintaining viability and function of said therapeutic cell population. In some embodiments, the therapeutic cell population comprises donor cells or recipient cells, and wherein the therapeutic cell population possesses an ability to induce apoptosis or inactivation of cells that are self-reactive. In some embodiments, the therapeutic cell population is selected from the group consisting of a differentiated cell expressing high growth factor production activity, a stem cell, and a cell or variety of cells expressing immune modulatory factors. In some embodiments, the differentiated cell expressing high growth factor production activity is endowed with an ability to produce high levels of growth factors by ex vivo manipulation. In some embodiments, the differentiated cell expressing high growth factor production activity naturally possesses the ability to express high levels of growth factors. In some embodiments, the stem cell is selected from the group consisting of embryonic stem cells, cord blood stem cells, placental stem cells, bone marrow stem cells, amniotic fluid stem cells, amniotic membrane stem cells, neuronal stem cells, circulating peripheral blood stem cells, mesenchymal stem cells, germinal stem cells, adipose tissue derived stem cells, exfoliated teeth derived stem cells, hair follicle stem cells, dermal stem cells, parthenogenically derived stem cells, reprogrammed stem cells, and side population stem cells. In some embodiments, the cell or variety of cells expressing immune modulatory factors resemble thymic cell populations.

In some embodiments, the matrix capable of maintaining viability and function of a therapeutic cell population is a macroporous polymer scaffold comprising porous walls that are essentially non-membranous, said porous walls consisting of microporous polymer struts defining macropores which are interconnected by macroporous passageways, said microporous polymer struts containing microporous passageways extending through said microporous polymer struts so that macropores on either side of a given microporous polymer strut are in communication through said given microporous polymer strut, said macropores having a mean diameter in a range from about 0.5 to about 3.5 mm, and said macroporous polymer scaffold having a porosity of at least 50%. In some embodiments, the matrix capable of maintaining viability and function of a therapeutic cell population is selected from the group consisting of irradiated bone, decellularized bone, decellularized placenta stroma, decellularized thymus, and decellularized organs. In some embodiments, the matrix capable of maintaining viability and function of a therapeutic cell population is made of a material in part or in whole selected from a group of materials comprised of glass, polystyrene, polypropylene, polyethylene, polyvinylidene fluoride, polyurethane, polyalginate, polysulphone, polyvinyl alcohol, acrylonitrile polymers, polyacrylamide, polycarbonate, polypentene, polypentane, nylon, magnetite, natural polysaccharide, modified polysaccharide, collagen, gelatin and modified gelatin.

In some embodiments, the layer of material with selective permeability is manufactured using biocompatible materials allowing for free diffusion of particles small than 1 micrometer. In some embodiments, the layer of material with selective permeability is manufactured using biocompatible materials that do not allow for substantial immune recognition of said cells inside said material.

In some embodiments, the implantable device may contain a porous substrate structure to which therapeutic cells are adherent, which can be implanted and explanted from a patient. In another embodiment, a medical device includes a porous substrate seeded with therapeutic cells, said device comprising of an additional layer allowing free exchange of molecules without cell escape. Said medical device is seeded with thymic medullary epithelial cells or progenitors of said thymic medullary epithelial cells. In conditions where tolerance to alloreactive donor cells is desired, the thymic medullary epithelial cells or progenitors thereof are derived from recipient cells. In conditions where tolerance to alloreactive recipient cells is desired, the thymic medullary epithelial cells or progenitors thereof are derived from donor cells.

Some embodiments disclosed herein relate to a method of treating an inflammatory condition. In some embodiments, the method includes selecting a population of cells producing soluble anti-inflammatory mediators, culturing said cells producing soluble anti-inflammatory mediators with a matrix in vitro so as to allow adherence of said cells to said matrix, overlaying a material with selective permeability over said cells and said matrix so as to allow for diffusion of soluble factors through said material but not escape of cells, and implanting said enclosed matrix containing therapeutic cells into a patient in need. In some embodiments, the inflammatory condition is characterized by elevated levels of inflammatory mediators, said mediators selected from a group comprising of: IL-1, IL-2, IL-5, IL-6, IL-8, IL-12, IL-15, IL-17, IL-18, IL-21, IL-23, TNF-alpha, Interferon-gamma, and TRANCE. In some embodiments, the inflammatory condition is selected from the group consisting of autoimmunity, transplant rejection, and aging. In some embodiments, the population of cells producing soluble anti-inflammatory mediators are selected from the group consisting of immature dendritic cells, lymphoid dendritic cells, alternatively activated macrophages, bone marrow mononuclear cells, mesenchymal stem cells, T regulatory cells, NKT cells, hematopoietic stem cells, cord matrix mononuclear cells, adipose tissue mononuclear cells, placental matrix mononuclear cells, cord blood mononuclear cells, and CD5 positive B cells. In some embodiments, the cell populations are autologous, allogeneic, or xenogeneic. In some embodiments, the cells are derived from one or a plurality of cell lines. In some embodiments, the enclosed matrix containing therapeutic cells is administered subcutaneously in a manner allowing for subsequent explantation.

Some embodiments disclosed here relate to a method of modifying an immune response. In some embodiments, the method includes selecting a population of cells producing soluble immune modulators, culturing said cells producing soluble immune modulators with a matrix in vitro so as to allow adherence of said cells to said matrix, overlaying a material with selective permeability over said cells and said matrix so as to allow for diffusion of soluble factors through said material but not escape of cells, and implanting said enclosed matrix containing therapeutic cells into a patient in need. In some embodiments, the immune response is an antibody mediated immune response or a cell mediated immune response.

DETAILED DESCRIPTION

Unless defined otherwise, all technical and scientific terms used herein have the same meaning as is commonly understood by one of ordinary skill in the art. All patents, applications, published applications, and other publications referenced herein are expressly incorporated by reference in their entireties unless stated otherwise. In the event that there is a plurality of definitions for a term herein, those in this section prevail unless stated otherwise.

The disclosure provides means of inducing thymic tolerance in an adult host through the generation of thymic medullary epithelial cells from donor tissue in the case of a solid organ transplant, and from recipient tissue in the case of a hematopoietic stem cell transplant.

In one embodiment, a method may include, for example, extraction of skin fibroblasts, retrodifferentiation of fibroblasts to cells possessing plasticity, and differentiating said cells possessing plasticity into cells possessing properties of the thymic medullary epithelium. Said thymic medullary epithelial cells can be utilized to induce tolerance in solid organ transplants by administration of donor-specific thymic medullary epithelial cells, or alternatively, in the situation of hematopoietic stem cell transplantation, recipient specific thymic medullary epithelial cells may be utilized to prevent graft versus host disease.

Means of dedifferentiating cells are known in the art and include treatment of cells with agents that act epigenetically, which may be utilized alone or in combination with inducible pluripotent stem cell techniques known in the art. In one embodiment cells are dedifferentiated by treatment with a DNA methyltransferase inhibitor said inhibitors include nucleoside analogues and non-nucleoside analogues. Exemplary nucleoside analogs include 5-Azacytidine (which may be used at a concentration of 100 nM to 10 µM), 5-Aza-2'-deoxycytidine (which may be used at a concentration of 100 nM to 10 µM), 5-Fluoro-2'-deoxycytidine (which may be used at a concentration of 100 nM to 10 µM), 5,6-Dihydro-5-azacytidine (which may be used at a concentration of 100 nM to 10 µM), and Zebularine (which may be used at a concentration of 1 µM to 10 mM). Exemplary non-nucleoside analogues include Hydralazine (which may be used at a concentration of 100 nM to 10 µM), Procainamide (which may be used at a concentration of 1000 nM to 10 µM), EGCG (which may be used at a concentration of 100 nM to 10 µM), Psammaplin A (which may be used at a concentration of 100 nM to 10 µM), MG98 (which may be used at a concentration of 100 nM to 10 µM), and RG108 (which may be used at a concentration of 100 nM to 10 µM).

Exemplary histone-deacetylase inhibitors include short chain fatty acids, hydroxamic acids, cyclic benzamides, cyclic tetrapeptides, and benzamides. Exemplary short chain fatty acids include Butyrate (which may be used at a concentration of 1 µM to 10 mM) and Valproic acid (which may be used at a concentration of 1 µM to 10 mM). Exemplary hydroxamic acids include m-carboxy cinnamic acid bishydroxamic acid (CBHA) (which may be used at a concentration of 100 nM to 10 µM), Oxamflatin (which may be used at a concentration of 100 nM to 10 µM), PDX 101 (which may be used at a concentration of 100 nM to 10 µM), Pyroxamide (which may be used at a concentration of 1 nM to 10 µM), Scriptaid (which may be used at a concentration of 100 nM to 10 µM), Suberoylanilide hydroxamic acid (SAHA) (which may be used at a concentration of 100 nM to 10 µM), Trichostatin A (TSA) (which may be used at a concentration of 1 nM to 10 µM), LBH589 (which may be used at a concentration of 1 nM to 10 µM), and NVP-LAQ824 (which may be used at a concentration of 1 nM to 10 µM). Exemplary cyclic tetrapeptides and benzamides include Apicidin (which may be used at a concentration of 1 nM to 10 µM), Depsipeptide (which may be used at a concentration of 100 nM to 10 µM), TPX-HA analogue (CHAP) (which may be used at a concentration of 1 nM to 10 µM), and Trapoxin (which may be used at a concentration of 1 nM to 10 µM). Exemplary Benzamides include CI-994 (N-acetyldinaline) (which may be used at a concentration of 100 nM to 10 µM) and MS-275 (which may be used at a concentration of 100 nM to 10 µM).

In one embodiment, a method may include, for example, generation of thymic tissue from skin cells that have been dedifferentiated. In addition to treatment with epigenetic mediators described above, one means of inducing dedifferentiation involves cytoplasmic transfer from undifferentiated cells to differentiated cells, otherwise defined as "reprogramming" of the cells. Methods of cytoplasmic transfer utilized for reprogramming of cells have been previously published with other cell systems and are incorporated by reference [11, 12]. In preferred embodiments of the above aspects, the cell expresses a combination of 5, 10, 25, 50, 75, 100, 150, 300, or more endogenous mRNA molecules or endogenous proteins that are not expressed by the cell from which said cytoplasm is extracted from the naturally-occurring undifferentiated cell. In another preferred embodiment, the cell expresses 1, 3, 5, 10, 25, 50, 100, or more endogenous mRNA molecules or endogenous proteins that are specific for one cell type and expresses 1, 3, 5, 10, 25, 50, 100, or more endogenous mRNA molecules or endogenous proteins that are specific for another cell type. In other preferred embodiments, the cell has a combination of 2, 5, 10, 25, 50, 75, 100, 150, 300, or more activities or phenotypes that are not exhibited in a naturally-occurring. In one embodiment a permeabilized fibroblast cell is exposed to a reprogramming media (e.g., a cell extract) under conditions that allow the removal of a factor from the nucleus or chromatin mass of the permeabilized cell or the addition of a factor to the nucleus or chromatin mass. The reprogrammed cell formed from this step is administered together with an immunological adjuvant to induce an immature phenotype to said cell.

In one preferred embodiment, the permeabilized cell is incubated with an interphase reprogramming media. Preferably, the nucleus in the permeabilized cell remains membrane-bounded, and the chromosomes in the nucleus do not condense during incubation with the interphase reprogramming media. In another preferred embodiment, a chromatin mass is formed from incubation of the permeabilized cell in a mitotic reprogramming media. In yet another preferred embodiment, the reprogrammed cell is incubated under conditions that allow the membrane of the reprogrammed cell to reseal prior to being administered to the mammal. Preferably, the permeabilized cell is from the mammal in need of that cell type. In another preferred embodiment, the permeabilized cell is formed by incubating an intact cell with a detergent, such as digitonin, or a bacterial toxin, such as Streptolysin O.

In some embodiments, at least 1, 5, 10, 15, 20, 25, 50, 75, 100, 150, 200, 300, or more mRNA or protein molecules are expressed in the reprogrammed cell that are not expressed in the donor or permeabilized cell. In another preferred embodiment, the number of mRNA or protein molecules that are expressed in the reprogrammed cell, but not expressed in the donor or permeabilized cell, is between 1 and 5, 5 and 10, 10 and 25, 25 and 50, 50 and 75, 75 and 100, 100 and 150, 150 and 200, or 200 and 300, inclusive. Preferably, at least 1, 5, 10, 15, 20, 25, 50, 75, 100, 150, 200, 300, or more mRNA or protein molecules are expressed in the donor or permeabilized cell that are not expressed in the reprogrammed cell. In yet another preferred embodiment, the number of mRNA or protein molecules that are expressed in the donor or permeabilized cell, but not expressed in the reprogrammed cell, is between 1 and 5, 5 and 10, 10 and 25, 25 and 50, 50 and 75, 75 and 100, 100 and 150, 150 and 200, or 200 and 300, inclusive. Preferably, the mRNA or protein molecules are specific for the cell type of the donor, permeabilized, or reprogrammed cell, such that the molecules are only expressed in cells of that particular cell type. In still another preferred embodiment, these mRNA or protein molecules are expressed in both the donor cell (i.e., the donor or permeabilized starting cell) and the reprogrammed cell, but the expression levels in these cells differ by at least 2, 5, 10, or 20-fold, as measured using standard assays (see, for example, Ausubel et al., Current Protocols in Molecular Biology, John Wiley & Sons, New York, 2000). In one embodiment, the size of the donor or permeabilized cell differs from that of the reprogrammed cell by at least 10, 20, 30, 50, 75, or 100%, as measured using standard methods. In another preferred embodiment, the volume of cytoplasm in the donor or permeabilized cell differs from that in the reprogrammed cell by at least 10, 20, 30, 50, 75, or 100%, based on standard methods. In yet another preferred embodiment, the reprogrammed cell has gained or lost an activity relative to the donor or permeabilized cell, such as production of matrix metalloproteases, angiogenic activity or chemotactic activity. In still other preferred embodiments, the reprogramming media is an interphase reprogramming media, such as an extract formed from cells synchronized in one or more of the phases of the cell cycle. In another embodiment, the reprogramming media is an extract formed from cells synchronized in mitosis or from unsynchronized cells. The reprogramming media is an extract from the cell type one wishes the donor or permeabilized cell to become, or the reprogramming media is a solution containing factors specific for the cell type one wishes the donor or permeabilized cell to become.

In one embodiment, the reprogramming media is modified by the enrichment or depletion of a factor, such as a DNA methyltransferase, histone deacetylase, histone, nuclear lamin, transcription factor, activator, repressor, growth factor, hormone, or cytokine. The reprogramming media may or may not contain exogenous nucleotides. In other embodiments, a chromatin mass in a reprogramming media or formed in a permeabilized cell is contacted with a vector having a nucleic acid encoding a gene of interest under conditions that allow homologous recombination between the nucleic acid in the vector and the corresponding nucleic acid in the genome of the chromatin mass, resulting in the alteration of the genome of the chromatin mass. Due to the lack of an intact plasma membrane and the lack of a nuclear membrane, a chromatin mass in a permeabilized cell may be easier to genetically modify than a naturally-occurring cell. Preferably, the chromatin mass or nucleus is purified from the reprogramming media prior to insertion into the recipient cell or cytoplast, or the reprogrammed cell is purified prior to administration into the mammal. Preferably, the donor or permeabilized cell is haploid (DNA content of n), diploid (2n), or tetraploid (4n), and the recipient cell is hypodiploid (DNA content of less than 2n), haploid, or enucleated.

Generation of pluripotent cells by other means are known in the art and described in the following works, which are incorporated by reference [13-15]. In some embodiments, pluripotent stem cells are treated to differentiate into thymic medullary epithelial cells. Said differentiation is accomplished by culture in approximately 10 µg/mL collagen IV precoated 6-well culture plates containing differentiation medium (mESC medium without leukemia inhibitory factor) and human fibroblast growth factor 7 at a concentration of approximately 20 ng/mL, human fibroblast growth factor 10 at a concentration of approximately 20 ng/mL, human bone morphogenetic protein 4 at a concentration of approximately 20 ng/mL, and human epithelial growth factor at a concentration of approximately 50 ng/mL. The medium and growth factors were changed every 3-4 days. Differentiated pluripotent cells are harvested at day 10 by treating the cells with approximately 2 mg/mL collagenase IV. Said differentiated thymic medullary epithelial cells may be utilized to induce transplant tolerance or reduction in transplant associated immune suppression in conditions of solid organ transplantation, in which case donor derived, or partially donor derived cells are utilized, or in the context of hematopoietic stem cell transplant in which prevention of graft versus host disease is required and as a resulted utilization of recipient derived, or partially recipient derived. In the context of autoimmunity thymic medullary epithelial cells are made to express autoantigens so as to promote tolerance to autoantigens stimulating autoimmunity. Autoantigens may be genetically engineered into pluripotent stem cells used to generate thymic medullary epithelial cells, or engineered directly into differentiated thymic medullary epithelial cells. In addition to genetically engineered, said autoantigens may be incorporated by means of protein delivery through protein transduction domains, by administering mRNA encoding for autoantigens, or by addition of autoantigens or peptides derived thereof so that pinocytosis may allow for uptake of said autoantigens.

In some embodiments, utilization of donor specific cells with veto activity encapsulated in a 3 dimensional matrix is described. A veto cell is a cell capable of specifically inducing T cell anergy, killing, inactivation or cytokine modulation in allogeneic T cells responding to said veto cell. One type of veto cell is a donor specific mesenchymal stem cell. In some embodiments, donor mesenchymal stem cells are seeded in a decellularized bone matrix, and said MSC are permitted to grow to take a 3 dimensional shape. Once said decellularized bone is significantly populated with said veto cells, said combination of decellularized bone matrix is either implanted directly into the patient in need of therapy, or coated with agents to allow for implantation. In some embodiments, a small implantable device is provided that is introduced subcutaneously or into a fat area of tissue. MSC conventionally are immune suppressive and it is known in the art that they promote tolerance. However, some embodiments include is the growth of MSC in three dimensional format allowing for formation of spheroids. The three dimensional structures are capable of maintaining or expanding MSC immune suppressive or veto activity. Specifically, one of the findings is the retention of MSC production of IL-10, TGF-beta and T regulatory cell stimulating ability after culture in 3 dimensional format. In some embodiments, the disclosure provides enhancement of IL-34 production through three dimensional structure, which is not achievable in standard 3 dimensional cultures. Some methods of the present disclosure can be practiced through administration of donor specific cells in situations where a veto effect is desired. Alternatively, in some embodiments, the method includes administration of third party cells for general non-specific immune modulation. In one specific embodiment, third-party cells are utilized in situations of transplantation where suppression of antibody mediated rejection is desired. In another embodiment, 3 dimensionally grown MSC spheroids are utilized for the generation of a tolerogenic response for the treatment of autoimmunity. Autoantigens may be added directly to the spheroid or can be genetically expressed in the MSC of the spheroid. Additionally, MSC may be engineered to express tolerogenic properties by culture conditions or genetic modification. One genetic modification disclosed herein is the transfection with Fas ligand, which has been demonstrated to induce donor specific tolerance. Other death associated ligands may be utilized such as perforin, granzyme, TRAIL, and components of the complement cascade. Transfection with tolerogenic genes may be performed to enhance immune modulatory effects of said MSC, for example transfection with IL-10, IL-20, IL-34, and TGF-beta. Said transfected genes may be controlled by use of specific promoters such as those inducible by orally administered agents. Additionally, transfection with In another embodiment, the production of 3 dimensional tolerogenic units is provided. Said tolerogenic units are comprised of multiple cell types that interact synergistically to provide enhancement of immune modulatory or veto properties. Specifically, MSC may be admixed with dendritic cell progenitors or immature dendritic cells. In this manner the MSC are cultured so as to provide inhibitory signals to dendritic cell progenitors so as to enhance ability of said progenitors to stimulate production of tolerogenic signals to T cells or stimulation of T regulatory cell production.

In some embodiments, tolerance is further promoted by enhancement of recipient colonization of donor tissue. Specifically, in the context of solid organ transplant, subsequent to intervention by either implantable devices containing donor derived thymic medullary epithelial cells or direct administration of thymic medullary epithelial cells, or intrathymic administration of thymic medullary epithelial cells, the recipient bone marrow is mobilized. G-CSF and GM-CSF are known to mobilize the production of granulocytes (primarily neutrophils) and macrophages, respectively, and also result in increased production of DC from the BM. Clinically, G-CSF and GM-CSF are used, for example, to decrease the incidence of infection (as manifested by febrile neutropenia) in patients with non-myeloid malignancies receiving myelosuppressive anti-cancer drugs, which are typically associated with a significant incidence of severe neutropenia and fever. Additionally, both of these drugs are approved clinically to prevent infections in patients receiving HSCT. Both G-CSF and GM-CSF are currently used in patients undergoing peripheral blood progenitor cell collection or therapy. Colony stimulating factors (CSFs), which stimulate the differentiation and/or proliferation of BM stem cells, have generated much interest because of their therapeutic potential for restoring depressed levels of hematopoietic stem cell-derived cells. CSFs in both human and murine systems have been identified and distinguished according to their activities. For example, granulocyte-CSF (G-CSF) and macrophage-CSF (M-CSF) stimulate the in vitro formation of neutrophilic granulocyte and macrophage colonies, respectively while GM-CSF and interleukin-3 (IL-3) have broader activities and stimulate the formation of both macrophage, neutrophilic and eosinophilic granulocyte colonies. IL-3 also stimulates the formation of mast, megakaryocyte and pure and mixed erythroid colonies (when erythropoietin is added). GM-CSF accelerates recovery of neutrophils and maintains functional capacity, yet has little demonstrable effect on platelet recovery. In contrast, IL-3 promotes a slower increase recovery in neutrophils and monocytes while accelerating the recovery of platelets. Thus, G-CSF and/or GM-CSF are used in some embodiments of the methods of the present disclosure. Sex steroid ablation together (sequentially or concurrently) with G-CSF and/or GM-CSF therapy results in an increase in the output from the BM of both lymphoid and myeloid cell, which in turn significantly improves both the short and long term outcomes for patients suffering, or likely to suffer from, infections. In another embodiment, the CSFs are administered 3-4 days after chemotherapy or radiation therapy to temporarily deplete reactive T cells. Clinical outcomes already associated with the use of the CSFs are also greatly enhanced by an interruption to sex steroid signaling. In particular, using some methods of the instant disclosure together with CSF's, allows for much greater infection control in patients receiving e.g., cancer radiation or chemotherapy. Additionally, if the immune system can be effectively and promptly reset, then increased dosages and/or frequency of chemotherapy drugs or radiation therapy may be used. This may occur with or without the introduction of allogeneic or autogenic HSC's which would further enhance the timely return of immune system functionality.

In some embodiments, combinations of immature dendritic cells together with mesenchymal stem cells are utilized to generate a tolerogenic milieu in order to treat or prevent autoimmunity. Said tolerogenic milieu may be generated in vivo or may be created by coculture of said immature dendritic cells and mesenchymal stem cells in vitro. In some embodiments cells of the tissue to which prevention or inhibition of autoimmunity is desired are added to the culture, said cells include endothelial cells, epithelial cells, dermal cells, endodermal cells, mesodermal cells, fibroblasts, osteocytes, chondrocytes, natural killer cells, dendritic cells, hepatic cells, pancreatic cells, stromal cells, salivary gland mucous cells, salivary gland serous cells, von Ebner's gland cells, mammary gland cells, lacrimal gland cells, ceruminous gland cells, eccrine sweat gland dark cells, eccrine sweat gland clear cells, apocrine sweat gland cells, gland of Moll cells, sebaceous gland cells. bowman's gland cells, Brunner's gland cells, seminal vesicle cells, prostate gland cells, bulbourethral gland cells, Bartholin's gland cells, gland of Littre cells, uterus endometrium cells, isolated goblet cells, stomach lining mucous cells, gastric gland zymogenic cells, gastric gland oxyntic cells, pancreatic acinar cells, paneth cells, type II pneumocytes, clara cells, somatotropes, lactotropes, thyrotropes, gonadotropes, corticotropes, intermediate pituitary cells, magnocellular neurosecretory cells, gut cells, respiratory tract cells, thyroid epithelial cells, parafollicular cells, parathyroid gland cells, parathyroid chief cell, oxyphil cell, adrenal gland cells, chromaffin cells, Leydig cells, theca interna cells, corpus luteum cells, granulosa lutein cells, theca lutein cells, juxtaglomerular cell, macula densa cells, peripolar cells, mesangial cell, blood vessel and lymphatic vascular endothelial fenestrated cells, blood vessel and lymphatic vascular endothelial continuous cells, blood vessel and lymphatic vascular endothelial splenic cells, synovial cells, serosal cell (lining peritoneal, pleural, and pericardial cavities), squamous cells, columnar cells, dark cells, vestibular membrane cell (lining endolymphatic space of ear), stria vascularis basal cells, stria vascularis marginal cell (lining endolymphatic space of ear), cells of Claudius, cells of Boettcher, choroid plexus cells, pia-arachnoid squamous cells, pigmented ciliary epithelium cells, nonpigmented ciliary epithelium cells, corneal endothelial cells, peg cells, respiratory tract ciliated cells, oviduct ciliated cell, uterine endometrial ciliated cells, rete testis ciliated cells, ductulus efferens ciliated cells, ciliated ependymal cells, epidermal keratinocytes, epidermal basal cells, keratinocyte of fingernails and toenails, nail bed basal cells, medullary hair shaft cells, cortical hair shaft cells, cuticular hair shaft cells, cuticular hair root sheath cells, hair root sheath cells of Huxley's layer, hair root sheath cells of Henle's layer, external hair root sheath cells, hair matrix cells, surface epithelial cells of stratified squamous epithelium, basal cell of epithelia, urinary epithelium cells, auditory inner hair cells of organ of Corti, auditory outer hair cells of organ of Corti, basal cells of olfactory epithelium, cold-sensitive primary sensory neurons, heat-sensitive primary sensory neurons, Merkel cells of epidermis, olfactory receptor neurons, pain-sensitive primary sensory neurons, photoreceptor rod cells, photoreceptor blue-sensitive cone cells, photoreceptor green-sensitive cone cells, photoreceptor red-sensitive cone cells, proprioceptive primary sensory neurons, touch-sensitive primary sensory neurons, type I carotid body cells, type II carotid body cell (blood pH sensor), type I hair cell of vestibular apparatus of ear (acceleration and gravity), type II hair cells of vestibular apparatus of ear, type I taste bud cells cholinergic neural cells, adrenergic neural cells, peptidergic neural cells, inner pillar cells of organ of Corti, outer pillar cells of organ of Corti, inner phalangeal cells of organ of Corti, outer phalangeal cells of organ of Corti, border cells of organ of Corti, Hensen cells of organ of Corti, vestibular apparatus supporting cells, taste bud supporting cells, olfactory epithelium supporting cells, Schwann cells, satellite cells, enteric glial cells, astrocytes, neurons, oligodendrocytes, spindle neurons, anterior lens epithelial cells, crystallin-containing lens fiber cells, hepatocytes, adipocytes, white fat cells, brown fat cells, liver lipocytes, kidney glomerulus parietal cells, kidney glomerulus podocytes, kidney proximal tubule brush border cells, loop of Henle thin segment cells, kidney distal tubule cells, kidney collecting duct cells, type I pneumocytes, pancreatic duct cells, nonstriated duct cells, duct cells, intestinal brush border cells, exocrine gland striated duct cells, gall bladder epithelial cells, ductulus efferens nonciliated cells, epididymal principal cells, epididymal basal cells, ameloblast epithelial cells, planum semilunatum epithelial cells, organ of Corti interdental epithelial cells, loose connective tissue fibroblasts, corneal keratocytes, tendon fibroblasts, bone marrow reticular tissue fibroblasts, nonepithelial fibroblasts, pericytes, nucleus pulposus cells, cementoblast/cementocytes, odontoblasts, odontocytes, hyaline cartilage chondrocytes, fibrocartilage chondrocytes, elastic cartilage chondrocytes, osteoblasts, osteocytes, osteoclasts, osteoprogenitor cells, hyalocytes, stellate cells (ear), hepatic stellate cells (Ito cells), pancreatic stelle cells, red skeletal muscle cells, white skeletal muscle cells, intermediate skeletal muscle cells, nuclear bag cells of muscle spindle, nuclear chain cells of muscle spindle, satellite cells, ordinary heart muscle cells, nodal heart muscle cells, Purkinje fiber cells, smooth muscle cells, myoepithelial cells of iris, myoepithelial cell of exocrine glands, reticulocytes, megakaryocytes, monocytes, connective tissue macrophages. epidermal Langerhans cells, dendritic cells, microglial cells, neutrophils, eosinophils, basophils, mast cell, helper T cells, suppressor T cells, cytotoxic T cell, natural Killer T cells, B cells, natural killer cells, melanocytes, retinal pigmented epithelial cells, oogonia/oocytes, spermatids, spermatocytes, spermatogonium cells, spermatozoa, ovarian follicle cells, Sertoli cells, thymus epithelial cell, and/or interstitial kidney cells.

Furthermore, in some embodiments, addition of growth factors or cytokines is performed in order to enhance tolerogenesis. Suitable growth factors useful for the practice of some methods disclosed herein include adrenomedullin (AM), angiopoietin (Ang), bone morphogenetic protein (BMP), brain-derived neurotrophic factor (BDNF), epidermal growth factor (EGF), erythropoietin (Epo), fibroblast growth factor (FGF), glial cell line-derived neurotrophic factor (GNDF), granulocyte colony stimulating factor (G-CSF), granulocyte-macrophage colony stimulating factor (GM-CSF), growth differentiation factor (GDF-9), hepatocyte growth factor (HGF), hepatoma derived growth factor (HDGF), insulin-like growth factor (IGF), migration-stimulating factor, myostatin (GDF-8), myelomonocytic growth factor (MGF), nerve growth factor (NGF), placental growth factor (PlGF), platelet-derived growth factor (PDGF), thrombopoietin (Tpo), transforming growth factor alpha (TGF-α), TGF-β, tumor necrosis factor alpha (TNF-α), vascular endothelial growth factor (VEGF), or a Wnt protein. Cytokines may be added to enhance tolerogenesis, said cytokines are required to endow properties onto the MSC to suppress DC maturation. In some embodiments MSC will be treated first with cytokines before co-culture. Suitable cytokines for the practice of some methods disclosed herein are selected from the group consisting of AM, Ang, BMP, BDNF, EGF, Epo, FGF, GNDF, G-CSF, GM-CSF, GDF-9, HGF, HDGF, IGF, migration-stimulating factor, GDF-8, MGF, NGF, PlGF, PDGF, Tpo, TGF-α, TGF-β, TNF-α, VEGF, or a Wnt protein; an interleukin; a soluble receptor for IL-1α, IL-1β, IL-1F1, IL-1F2, IL-1F3, IL-1F4, IL-1F5, IL-1F6, IL-1F7, IL-1F8, IL-1F9, IL-2, IL-3, IL-4, IL-5, IL-6, IL-7, IL-8, IL-9, IL-10, IL-11, IL-12 35 kDa alpha subunit, IL-12 40 kDa beta subunit, IL-13, IL-14, IL-15, IL-16, IL-17A, IL-17B, IL-17C, IL-17D, IL-17E, IL-17F isoform 1, IL-17F isoform 2, IL-18, IL-19, IL-20, IL-21, IL-22, IL-23 p19 subunit, IL-23 p40 subunit, IL-24, IL-25, IL-26, IL-27B, IL-27-p28, IL-28A, IL-28B, IL-29, IL-30, IL-31, IL-32, IL-33, IL-34, IL-35, IL-36α, IL-36β, IL-36γ; an interferon (IFN); a soluble receptor for IFN-α, IFN-β, IFN-γ, IFN-.lamda.1, IFN-.lamda.2, IFN-.lamda.3, IFN-K, IFN-ε, IFN-κ, IFN-τ, IFN-δ, IFN-ζ, IFNω, or IFN-υ; insulin or proinsulin; a receptor for insulin; leptin (LEP). In some embodiments cytokines and/or growth factors are administered to said cells continually through a micropump connected to an encapsulation device that houses said tolerogenic cells. Particular encapsulation devices of interest may be obtained from U.S. Pat. Nos. 5,725,854; 5,849,285; 5,759,534; 5,843,430; 5,958,404; and 6,149,907.

Provided herein is a composite cellular tolerogenic vaccine comprising one or more types of cells, and decellularized placental vascular scaffold, or other types of scaffolds including extracellular matrix from tissues suitable for cellular seeding. Decellularized placental vascular scaffold comprises substantially intact placental vasculature matrix; that is, the structure of the vasculature of the placenta from which the matrix is obtained is substantially preserved during decellularization and subsequent production of the cellular composite tolerogenic vaccine. In certain embodiments, once the cellular composite vaccine is generated, the cells are irradiated and implanted with tolerogenic adjuvant or without adjuvant to stimulate tolerance to auto or allo antigens.

In one embodiment methods of the present disclosure include obtaining a human placenta that is recovered shortly after its expulsion after normal birth, or after a Caesarian section. The placenta is recovered from a patient after informed consent and after a complete medical history of the patient is taken and is associated with the placenta. Preferably, the medical history continues after delivery. Such a medical history can be used to coordinate subsequent use of the placenta or the stem cells harvested therefrom. For example, human placental stem cells can be used, in light of the medical history, for personalized medicine for the infant associated with the placenta, or for parents, siblings or other relatives of the infant. The umbilical cord blood and placental blood are removed, and can be used for other purposes or discarded. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., by LifeBank USA, Cedar Knolls, N.J. Preferably, the placenta is gravity drained without further manipulation so as to minimize tissue disruption during cord blood recovery. Typically, a placenta is transported from the delivery or birthing room to another location, e.g., a laboratory, for recovery of cord blood and collection of stem cells by, e.g., perfusion or tissue dissociation. The placenta is preferably transported in a sterile, thermally insulated transport device (maintaining the temperature of the placenta between about 20° C. to about 28° C.), for example, by placing the placenta, with clamped proximal umbilical cord, in a sterile zip-lock plastic bag, which is then placed in an insulated container. In another embodiment, the placenta is transported in a cord blood collection kit substantially as described in pending U.S. Pat. No. 7,147,626. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta. The placenta can be stored under sterile conditions and at either room temperature or at a temperature of 5° C. to 25° C. The placenta may be stored for a period of for a period of four to twenty-four hours, up to forty-eight hours, or longer than forty eight hours, prior to perfusing the placenta to remove any residual cord blood. In one embodiment, the placenta is harvested from between about zero hours to about two hours post-expulsion. The placenta is preferably stored in an anticoagulant solution at a temperature of 5° C. to 25° C. Suitable anticoagulant solutions are well known in the art, e.g., a solution of heparin or warfarin sodium. In a preferred embodiment, the anticoagulant solution comprises a solution of heparin (e.g., 1% w/w in 1:1000 solution). The exsanguinated placenta is preferably stored for no more than 36 hours before placental stem cells are collected. Said stem cells may be used as a source of mesenchymal stem cells for the practice of certain methods disclosed herein.

The use of decellularized placental matrix, to be subsequently seeded with immune regulatory cells including thymic medullary epithelial cells, immature dendritic cells, monocytic progenitors, and mesenchymal stem cells is disclosed. Particularly, the use of decellularized placenta allows for formulation of distinct tolerogenic units that may be seeded with allogeneic or autologous antigens in order to promote tolerogenesis. In one embodiment the means of decellularization is performed by the administration of a solution effective to lyse native placental cells. Preferably, the solution is an aqueous hypotonic or low ionic strength solution formulated to effectively lyse the cells. In certain embodiments, the aqueous hypotonic solution is, e.g. deionized water or an aqueous hypotonic buffer. In specific embodiments, the aqueous hypotonic buffer contains one or more additives that provide sub-optimal conditions for the activity of one or more proteases, for example collagenase, which may be released as a result of cellular lysis. Additives such as metal ion chelators, for example 1,10-phenanthroline and ethylenediaminetetraacetic acid (EDTA), create an environment unfavorable to many proteolytic enzymes. In other embodiments, the hypotonic lysis solution is formulated to eliminate or limit the amount of divalent cations, e.g., calcium and/or zinc ions, available in solution, which would, in turn, reduce the activity of proteases dependent on such ions.

It is important to prevent formation of viscous liquids during the decellularlization process, accordingly, in some embodiments, decellularization of placental tissue includes treatment of the tissue with one or more nucleases, e.g., effective to inhibit cellular metabolism, protein production and cell division without degrading the underlying collagen matrix. Nucleases that can be used for digestion of native cell DNA and RNA include either or both of exonucleases or endonucleases. Suitable nucleases for decellularization are commercially available. For example, it is known that exonucleases that effectively inhibit cellular activity include DNAase I (SIGMA Chemical Company, St. Louis, Mo.) and RNAase A (SIGMA Chemical Company, St. Louis, Mo.) and endonucleases that effectively inhibit cellular activity include EcoRI (SIGMA Chemical Company, St. Louis, Mo.) and Hind III (SIGMA Chemical Company, St. Louis, Mo.). For the practice of certain methods disclosed herein, selected nucleases may be contained in a physiological buffer solution which contains ions that are optimal for the activity of the nuclease, e.g., magnesium salts or calcium salts. It is also preferred that the ionic concentration of the buffered solution, the treatment temperature and the length of treatment are selected to assure the desired level of effective nuclease activity. The buffer is preferably hypotonic to promote access of the nucleases to cell interiors. In certain embodiments, the one or more nucleases comprise DNAase I and RNAase A. Preferably, the nuclease degradation solution contains about 0.1 microgram/mL to about 50 microgram/mL, or about 10 microgram/mL, of the nuclease DNAase I, and about 0.1 microgram/mL to about 10 microgram/mL, preferably about 1.0 microgram/mL, of RNAase A. The placental tissue may be decellularized by application of the foregoing enzymes at a temperature of about 20° C. to 38° C., preferably at about 37° C., e.g., for about 30 minutes to 6 hours. It is known in the art that the process of decellularization is associated with creation of tissue debris, therefore the placental tissue matrix in certain embodiments is washed in a wash solution to assure removal of cell debris which may include cellular protein, cellular lipids, and cellular nucleic acid, as well as any extracellular debris. Removal of this cellular and extracellular debris reduces the likelihood of the transplant tissue matrix eliciting an adverse immune response from the recipient upon implant. For example, the tissue may be washed one or more times with a wash solution, wherein the wash solution is, e.g., PBS or Hanks' Balanced Salt Solution (HBSS). The composition of the balanced salt solution wash, and the conditions under which it is applied to the transplant tissue matrix may be selected to diminish or eliminate the activity of proteases or nucleases utilized during the decellularization process. In specific embodiments, the wash solution does not contain magnesium or calcium, e.g. magnesium salts or calcium salts, and the washing process proceeds at a temperature of between about 2° C. and 42° C., e.g., most preferably at about 4° C. The transplant tissue matrix may be washed, e.g., incubated in the balanced salt wash solution for up to 1, 2, 3, 4, 5, 6, 7, 8, 9, 10, 11 or 12 days, e.g., with changes in wash solution every 13 days. Optionally, an antibacterial, an antifungal or a sterilant or a combination thereof, may be included in the wash solution to protect the transplant tissue matrix from contamination with environmental pathogens. Washing may be performed by soaking the placental tissue with or without mild agitation.

To allow for large scale production, it may not be feasible to seed the tissue the same day that the cells are added. Accordingly, the placental tissue matrix, once decellularized, can be preserved by cryopreservation. Techniques of cryopreservation of tissue are well known in the art. See, e.g., Brockbank, K. G. M., "Basic Principles of Viable Tissue Preservation," In: Transplantation Techniques and Use of Cryopreserved Allograft Cardiac Valves and Vascular Tissue, D. R. Clarke (ed.), Adams Publishing Group, Ltd., Boston. pp 9-23 (discussing cryopreservation of tissues and organs). The tissue matrix, whether or not having been cryopreserved, in certain embodiments is treated to enhance the adhesion and inward migration of the allogeneic or autologous cells, in vitro, which will be used to repopulate the transplant tissue. In certain embodiments, attachment of autologous or allogeneic cells to decellularized placental vascular scaffold may be increased, e.g., by contacting the placental vascular scaffold with serum (human or fetal bovine, maximal binding with 1% serum) and/or purified fibronectin, e.g., in culture medium in which the decellularized placental vascular scaffold is placed, e.g., in preparation for repopulation with allogeneic or autologous cells. Each of the two homologous subunits of fibronectin has two cell recognition regions, including one comprising the Arg-Gly-Asp (RGD) sequence. A second site, binding glycosaminoglycans, acts synergistically and appears to stabilize the fibronectin-cell interactions mediated by the RGD sequence. Additionally, platelet rich plasma, or platelet lysate may be utilized. As such, in a specific embodiment, the decellularized placental vascular scaffold is contacted with both fibronectin and a glycosaminoglycan, e.g., heparin, for a period effective for binding of the fibronectin to surfaces of the placental vascular scaffold to be repopulated with allogeneic or autologous cells. The fibronectin, and optionally glycosaminoglycan, can be included within a physiologically-acceptable buffer or culture medium, e.g., sodium phosphate/glycerin/bovine serum albumin and Dulbecco's Modified Eagle's Medium (DMEM) (e.g., GIBCO). The buffer or culture medium is preferably maintained at a physiologically acceptable pH, e.g., about 6.8 to 7.6. Fibronectin may be obtained from human blood, processed to limit contamination with virus, or may be obtained from commercial sources. The concentration of fibronectin and/or glycoprotein may range from about 1 microgram/mL to about 100 microgram/mL, e.g., about 10 microgram/mL. The preferred weight ratio of fibronectin to heparin is about 100:1 to about 1:100, or about 10:1 to about 1:10, e.g., 10:1 fibronectin:glycosaminoglycan, e.g. heparin. The decellularized placental vascular scaffold may be contacted with, e.g., treated with, one or more compositions that act, e.g., to enhance cell chemotaxis, increasing the rate of directional movement along a concentration gradient of the substance in solution. With respect to fibroblast cells, fibroblast growth factor, platelet-derived growth factor, transforming growth factor-beta (TGF-β), fibrillar collagens, collagen fragments, and fibronectin are chemotactic.

As provided herein, a matrix that is capable of maintaining viability of a cell is a matrix that is provides an environment for cell to be able to survive. Such a matrix is described in various aspects and embodiments herein. Furthermore, as described herein, a matrix that is capable of maintaining function of a cell is a matrix that provides an environment for cellular functioning to take place. Such a matrix is described in various aspects and embodiments herein.

In a specific, preferred embodiment, the placenta is decellularized as follows. Placental tissue, e.g., a whole placenta or lobule (cotyledon) of a placenta, from which blood has been removed is first frozen at −20° C. to −180° C., e.g., about −80° C., e.g., for about 24 hours. The tissue is then thawed at about 4° C. overnight. The thawed tissue is then digested with 0.1% trypsin at room temperature for 2 hours to 24 hours to produce digested placental tissue at 25° C. to about 37° C. In this digestion, and in subsequent steps, solution is passed through the placental vasculature (perfusion decellularization). The digested tissue is then treated sequentially with 1%, 2% and 3% Triton-X100 for 24 hours each at room temperature or about 25° C. The Triton-X100 treatments are then followed by treatment of the tissue with 0.1% SDS-PBS for 24 h at room temperature or at about 25° C., after which the cellular material is substantially removed. The tissue is then extensively washed with 1-10 changes of phosphate buffered saline (PBS), followed by treatment with DNase I (150 U/mL) for 1 hour at room temperature, each step at room temperature or about 25° C. Finally, the remaining decellularized placental vascular scaffold is again extensively washed at room temperature or about 25° C. with PBS+1% antibiotics (penicillin+streptomycin), optionally dried, and preserved at 4° C.

Following decellularization, the resulting placental vascular scaffold may be combined with one or more synthetic matrices, e.g., synthetic polymers. In a specific embodiment, the synthetic matrix stabilizes the three-dimensional structure of the placental vascular scaffold, e.g., to facilitate production of the organoid. In another specific embodiment, said synthetic matrix comprises a polymer or a thermoplastic. In a more specific embodiment, said synthetic matrix is a polymer or a thermoplastic. In more specific embodiments, said thermoplastic is polycaprolactone, polylactic acid, polybutylene terephthalate, polyethylene terephthalate, polyethylene, polyester, polyvinyl acetate, or polyvinyl chloride. In other more specific embodiments, said polymer is polyvinylidine chloride, poly(o-carboxyphenoxy)-p-xylene) (poly(o-CPX)), poly(lactide-anhydride) (PLAA), n-isopropyl acrylamide, acrylamide, pent erythritol diacrylate, polymethyl acrylate, carboxymethylcellulose, or poly (lactic-co-glycolic acid) (PLGA). In another more specific embodiment, said polymer is polyacrylamide. In some embodiments it is at this stage the placental decellularized tissue is seeded with immune modulatory cells. In any of the above embodiments, the placental vascular scaffold may be decellularized by passage of any of the decellularizing and/or wash components described above through the placental vasculature, e.g., through the placental arteries and/or placental vein. Methods of perfusing through the placental vasculature are described, e.g., in U.S. Pat. No. 8,057,788, the disclosure of which is hereby incorporated by reference in its entirety.

Immune modulatory stem cells may be derived from other stem cell sources besides MSC, however in the case of MSC, said cells express one or more of the following markers: STRO-1, CD105, CD54, CD106, HLA-I markers, vimentin, ASMA, collagen-1, fibronectin, LFA-3, ICAM-1, PECAM-1, P-selectin, L-selectin, CD49b/CD29, CD49c/CD29, CD49d/CD29, CD61, CD18, CD29, thrombomodulin, telomerase, CD10, CD13, STRO-2, VCAM-1, CD146, and THY-1. Further embodiments encompass methods wherein mesenchymal stem cells do not express substantial levels of HLA-DR, CD117, and CD45. Further embodiments encompass methods wherein mesenchymal stem cells are derived from the group consisting of bone marrow, adipose tissue, umbilical cord blood, placental tissue, peripheral blood mononuclear cells, differentiated embryonic stem cells, and differentiated progenitor cells. Further embodiments encompass methods wherein germinal stem cells express markers selected from the group consisting of Oct4, Nanog, Dppa5 Rbm, cyclin A2, Tex18, Stra8, Daz1, beta1- and alpha6-integrins, Vasa, Fragilis, Nobox, c-Kit, Sca-1 and Rex1.

Further embodiments encompass methods wherein adipose tissue derived stem cells express markers are selected from the group consisting of CD13, CD29, CD44, CD63, CD73, CD90, CD166, Aldehyde dehydrogenase (ALDH), and ABCG2. Further embodiments encompass methods wherein adipose tissue derived stem cells are a population of purified mononuclear cells extracted from adipose tissue capable of proliferating in culture for more than 1 month. Further embodiments encompass methods wherein exfoliated teeth derived stem cells express markers selected from the group consisting of: STRO-1, CD146 (MUC18), alkaline phosphatase, MEPE, and bFGF. Further embodiments encompass methods wherein hair follicle stem cells express markers selected from the group consisting of cytokeratin 15, Nanog, and Oct-4. Further embodiments encompass methods wherein hair follicle stem cells are capable of proliferating in culture for a period of at least one month. Further embodiments encompass methods wherein hair follicle stem cells secrete one or more of the following proteins when grown in culture: basic fibroblast growth factor (bFGF), endothelin-1 (ET-1) and stem cell factor (SCF). Further embodiments encompass methods wherein dermal stem cells express markers selected from the group consisting of CD44, CD13, CD29, CD90, and CD105. Further embodiments encompass methods wherein dermal stem cells are capable of proliferating in culture for a period of at least one month. Further embodiments encompass methods wherein parthenogenically derived stem cells are generated by addition of a calcium flux inducing agent to activate an oocyte followed by enrichment of cells expressing markers selected from the group consisting of SSEA-4, TRA 1-60 and TRA 1-81. Further embodiments encompass methods wherein reprogrammed stem cells are selected from the group consisting of cells subsequent to a nuclear transfer, cells subsequent to a cytoplasmic transfer, cells treated with a DNA methyltransferase inhibitor, cells treated with a histone deacetylase inhibitor, cells treated with a GSK-3 inhibitor, cells induced to dedifferentiate by alteration of extracellular conditions, and cells treated with various combination of the mentioned treatment conditions. Further embodiments encompass methods wherein nuclear transfer comprises introducing nuclear material to a cell substantially enucleated, said nuclear material deriving from a host whose genetic profile is sought to be dedifferentiated. Further embodiments encompass methods wherein cytoplasmic transfer comprises introducing cytoplasm of a cell with a dedifferentiated phenotype into a cell with a differentiated phenotype, such that said cell with a differentiated phenotype substantially reverts to a dedifferentiated phenotype. Further embodiments encompass methods wherein DNA demethylating agent is selected from the group consisting of 5-azacytidine, psammaplin A, and zebularine. Further embodiments encompass methods wherein histone deacetylase inhibitor is selected from the group consisting of valproic acid, trichostatin-A, trapoxin A and depsipeptide. Further embodiments encompass methods wherein cells are identified based on expression multidrug resistance transport protein (ABCG2) or ability to efflux intracellular dyes such as rhodamine-123 and or Hoechst 33342. Further embodiments encompass methods wherein cells are derived from tissues such as pancreatic tissue, liver tissue, smooth muscle tissue, striated muscle tissue, cardiac muscle tissue, bone tissue, bone marrow tissue, bone spongy tissue, cartilage tissue, liver tissue, pancreas tissue, pancreatic ductal tissue, spleen tissue, thymus tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue, lung tissue, testicular tissue, ovarian tissue, prostate tissue, connective tissue, endocrine tissue, and mesentery tissue.

In some embodiments, said tolerogenic unit generated from coculture of mesenchymal stem cells, or other stem cells, together with immature dendritic cells, and/or cytokines and growth factors are utilized as in vivo factories of immunemodulatory exosomes. Alternatively, tolerogenic exosomes generated from said immune modulatory units maybe collected ex vivo and subsequently utilized for induction of antigen specific tolerance.

Exosomes are nanoparticles (40-100 nm) in size that possess highly defined homogeneous characteristics [16]. Originally thought to be a by-product of cell protein turnover [17], these particles are becoming appreciated as a critical means of intracellular communication in areas ranging from neurotransmission [18], to immune modulation [17], to infectious disease [19]. Compared with other secreted vesicles, exosomes have much better defined biophysical and biochemical properties, specifically, they have a diameter of 40-100 nm (with a density in sucrose of 1.13-1.19 g/ml, and can be sedimented at 100,000 g [16]. Their membranes are enriched in cholesterol, sphingomyelin and ceramide, and are known to contain lipid rafts. Exosomes were originally discovered as a means of exportation of the transferrin receptor during sheep reticulocyte maturation [20]. In recent years an explosion of interest in exosomes has occurred, with a wide variety of cells being reported to secrete these nanoparticles ranging from T cells [21, 22], B cells [23, 24], dendritic cells [25, 26], tumor cells [27, 28], neurons [29, 30], oligodendrocytes [31], and placental cells [32]. It is believed that exosomes play fundamental role in immune escape of the "fetal allograft" [33]. Endometrial regenerative cells (ERC) are believed to be precursors of MSC that development into the maternal portion of the placenta. Given the high angiogenic activity of ERC, as well as their ability to induce therapeutic effects in xenogeneic immune competent models [34], some embodiments of the present disclosure include the utilization of ERC exosomes as a non-cellular method of inducing immune modulatory effects that are present when ERC are administered therapeutically. In another embodiment, exosomes from other stem cells may be utilized for immunotherapeutic purposes.

Immunological functions of exosomes were first identified in B cells [35], through studies demonstrating that these cells contain a late endocytic compartment, called MIIC (major histocompatibility complex [MHC] class II-enriched compartment), that harbors newly synthesized MHC class II molecules in transit to the plasma membrane. It was found that the MIIC compartment would fuse with the plasma membrane, but instead of the MHC II molecules becoming membrane bound, some would be found in the soluble fraction. These particles, which the investigators termed "exosomes" in reference to original work on reticulocytes [20], were demonstrated to possess a distinct surface composition as compared to the plasma membrane. Interestingly, in the exosomes, a high concentration of MHC I and II, as well as antigen were found. In 2004 our group filed Canadian Patent #2453198 entitled "QUANTIFICATION AND GENERATION OF IMMUNE SUPPRESSIVE EXOSOMES". To our knowledge these were the first data demonstrating that in certain contexts, exosomes may suppress the immune system. These data, which were subsequently published, demonstrated that exosomes from prostate cancer patients suppress T cell activation in an MHC I and Fas ligand dependent manner [36]. In some embodiments, methodologies used for purification of immune suppressive exosomes from tumor cells, incorporated by reference, are applied to conditioned media of stem cells, specifically of mesenchymal stem cells, and more specifically of endometrial regenerative cells, in order to isolate, concentrate and therapeutically administer exosomes derived from stem cells for immune modulatory purposes.

We have previously published that immature dendritic cells promote induction of tolerance [37], and that administration of this "tolerogenic vaccine" is capable of suppressing autoimmunity in an in vivo manner [38]. Given the notion that mature dendritic cell exosomes are immune stimulatory [39, 40], it was logical to investigate whether exosomes generated from "tolerogenic" dendritic cells may prevent immune activation. Indeed Ruffner et al. demonstrated that dendritic cells treated with IL-10 to block maturation secreted exosomes that inhibited immune response in an antigen-specific manner in the delayed type hypersensitivity system [41]. Furthermore, they demonstrated that the immune inhibiting effect of the IL-10-treated exosome required presence of CD80 and CD86 on the exosome. Yang et al. used donor-strain derived exosomes from immature dendritic cells to enhance allograft survival in a F334>Wistar intestinal allotransplantation model [42]. The researchers demonstrated that as little as 20 ug of donor (but not recipient) derived exosomes was capable of causing a more than double increase in graft survival. Similar prolongation of graft survival using donor immature dendritic cell isolated exosomes was observed in a cardiac allograft model by another group [43]. Kim et al. demonstrated that exosomes mediating effects of tolerogenic DC were on average 75 nm in size [44] and depended on FasL for mediation of suppressive effects on T cells using KLH recall response as an output assay. Exosome production from tolerogenic dendritic cells may be labeled by some as "artifactual", therefore, let us examine the relevance of exosomes in naturally-occurring examples of immunological tolerance. In some embodiments, techniques used to enhance immune suppressive activities of exosomes secreted by other cells are applied to stem cells, mesenchymal stem cells and endometrial regenerative cells in order to augment immune suppressive activities. For example, ERC may be treated with compounds that inhibit inflammatory signals, such as IL-10, in order to generate populations of ERC that produce exosomes with enhanced immune modulatory activities. Conversely, in other aspects, exosomes may be purified from ERC that are growing under standard culture conditions.

The term "fetal allograft" has been often used to refer to the ability of the genetically mismatched fetus to survive within the mother. Although the fetal maternal barrier was originally believed to act as a barrier to trans-placental traffic, this was later found to be erroneous. Murine embryo transfer experiments utilizing wild-type embryos transferred into pseudopregnant LacZ mothers demonstrated extensive maternal cell infiltration, persisting into adulthood [45]. Conversely fetal cells have been demonstrated to enter maternal circulation and play both therapeutic [46] and pathological roles [47] depending on context. It has become apparent that during pregnancy, local and systemic immune deviation occurs [48], and that failure to induce this "natural immune modulation" is associated with recurrent spontaneous abortions [49, 50]. It appears that exosome production is associated, at least in part, with reprogramming of the maternal immune system to accommodate the allogeneic fetus. In 2005, Frangsmyr et al. reported that fetal syncytiotrophoblast cells express intracellular Fas ligand (FasL), which is secreted as exosomal particles into systemic circulation. They also found similar FasL expressing exosomes to be generated by cultured trophoblast cells [51]. As mentioned above in the examples of cancer-derived exosomes, and tolerogenic dendritic cell derived exosomes, FasL expression on these particles is associated with killing of activated T cells. Therefore, it may be conceptually possible that in physiological situations in which tolerogenesis is required, exosomes bearing antigen on MHC I/II, with or without costimulation, transmit a signal to the T cells that activate them antigen-specifically. The activated T cell then receives a "death signal" from the FasL, causing specific killing of the T cell clones that pose a threat to the exosome-producing entity. A functional association between FasL expression, exosome concentration, and suppression of T cell activity as assessed by TCR-zeta chain activity was demonstrated in Doug Taylor's group. Furthermore, they observed that preterm deliveries, which are associated with higher degree of maternal-antifetal immunity, are associated with lower concentrations of FasL expressing exosomes [52]. Pregnancy-associated exosomes appear to possess multiple means of modulating T cell responses. For example, the same group demonstrated that the "co-inhibitory" molecule PD1 ligand, is also expressed on pregnancy derived exosomes in circulation and that the inhibition of T cell activity was occurring not only at the CD4 level but more profoundly on CD8 T cells [53]. Another group demonstrated that pregnancy-associated exosomes, and those isolated from syncytiotrophoblasts express high levels of MHC class I chain-related proteins A and B (MICA/B) [33]. This protein specifically binds to the natural killer activating receptor NKG2D and suppresses NK activity. Interestingly it was found that culture of peripheral blood mononuclear cells from non-pregnant women with exosomes from pregnant women resulted in downregulation of NKG2D expression, as well as suppressed NK activity. Additionally, pregnant women had substantially lower expression of NKG2D compared to non-pregnant controls. The same group subsequently found that pregnancy-associated exosomes express a second family of human NKG2D ligands, the UL-16 binding proteins (ULBP), which inhibit not only NK cell activity, but also CD8 T cells and gamma delta T cells [54]. The potent immune modulation associated with pregnancy has been reported to inhibit clinical autoimmunity in conditions such as rheumatoid arthritis, [55] and multiple sclerosis [56]. Interestingly, a study in the animal model of multiple sclerosis, experimental autoimmune encephalomyelitis, demonstrated that exosomes produced during pregnancy may be responsible for the therapeutic effects on autoimmunity [57]. Thus in the situation of "natural tolerance" induced by pregnancy, it appears that exosomes play a role in temporary down-modulation of maternal responses. The potential of tumor-derived exosomes to kill/inactivate T cells through a Fas-FasL mechanism has been demonstrated in ovarian cancer [58], prostate cancer [36], and melanoma [22]. However, numerous other means of immune modulation have been ascribed to cancer-derived exosomes. For example, Valenti et al. showed that exosomes from melanoma and cervical cancer patients can "reprogram" monocytes into myeloid derived suppressor cells [59]. These cells play an important role in protecting tumor cells from T cell mediated immunity through secretion of suppressive factors such as PGE2, nitric oxide, arginase, and production of reactive oxygen intermediates [60].

Another "indirect" means by which tumor exosomes contribute to immune evasion is through the generation of T regulatory cells [61]. It was recently demonstrated by Whiteside's group that co-culture of tumor derived exosomes with naïve T cells, under certain conditions, would lead to potent generation of T regulatory cells that could suppress other T cells from activation. This concept of "infectious tolerance" has been described in the area of tumor immunotherapy with little mechanistic knowledge. Yet another mechanism of tumor exosome immune suppression is through the production of free adenosine via the enzyme CD73, which has been demonstrated to be expressed highly on tumor-derived exosomes [27]. Induction of oral tolerance appears to be associated with generation of T regulatory/Th3 cells that are specific to food-borne antigens [62]. While clinical trials of oral tolerance in rheumatoid arthritis [63], and multiple sclerosis [64, 65], have shown some promising results, to date, efficacy has not been able to meet the bar required by regulators for registration. By understanding biological mechanisms involved in induction of this innocuous form of tolerance, it may be feasible to develop therapeutic modalities to increase efficacy. It was demonstrated that subsequent to feeding with a nominal antigen, plasma-circulating exosomes containing MHC II and the antigen could be captured. In vitro culture of these exosomes revealed ability to antigen-specifically suppress T cell activation [66]. Using a murine allergy model it was demonstrated that protection from allergy could be transferred via exosomes collected from mice that had been fed the allergen orally [67]. These data suggest that tolerance induction may be occurring through the generation of tolerogenic exosomes as had been seen in the case of pregnancy and cancer in the previous sections. In certain embodiments, exosomes from stem cells are purified based on expression of certain markers that have been associated with naturally-occurring immune suppression induced by exosomes secreted by non-stem cells. In one embodiment, exosomes are generated in a means that causes preferential production of CD73 expressing exosomes. Specifically, ERC are cultured under conditions optimized for production of CD73 expressing exosomes by variation of culture conditions. In one specific embodiment, 10 ng/ml of IL-10 is added to ERC in tissue culture. Culture of ERC has been described in the paper Meng et al. [68], and incorporated by reference. Specific culture conditions and clinical use of ERC has been previously described in conditions such as congestive heart failure [69] and spinal cord injury [70]. Additionally, other cells may be used as a source of stem cells capable of producing exosomes. Cord blood cells useful for therapeutic applications have been described by us and are incorporated by reference [71].

EMBODIMENTS

While various aspects and embodiments have been disclosed herein, other aspects and embodiments will be apparent to those skilled in the art. Various exemplary embodiments of the disclosure can be described according to the following embodiments.

Some embodiments disclosed herein related to an implantable device including a therapeutic cell population, a matrix capable of maintaining viability and function of said therapeutic cell population, and a layer of material with selective permeability surrounding said matrix capable of maintaining viability and function of said therapeutic cell population.

In some embodiments, the therapeutic cell population is selected from the group consisting of a differentiated cell expressing high growth factor production activity, a stem cell, and a cell or variety of cells expressing immune modulatory factors. In some embodiments, the differentiated cell expressing high growth factor production activity is endowed with ability to produce high levels of growth factors by ex vivo manipulation. In some embodiments, the differentiated cell expressing high growth factor production activity naturally possesses the ability to express high levels of growth factors. In some embodiments, the stem cell is selected from the group of stem cells consisting of embryonic stem cells, cord blood stem cells, placental stem cells, bone marrow stem cells, amniotic fluid stem cells, amniotic membrane stem cells, neuronal stem cells, circulating peripheral blood stem cells, mesenchymal stem cells, germinal stem cells, adipose tissue derived stem cells, exfoliated teeth derived stem cells, hair follicle stem cells, dermal stem cells, parthenogenically derived stem cells, reprogrammed stem cells, and side population stem cells. In some embodiments, the cell or variety of cells expressing immune modulatory factors resemble thymic cell populations.

In some embodiments, the matrix capable of maintaining viability and function of a therapeutic cell population is a macroporous polymer scaffold including porous walls that are essentially non-membranous, the porous walls including of microporous polymer struts defining macropores which are interconnected by macroporous passageways. In some embodiments, the microporous polymer struts contain microporous passageways extending through the microporous polymer struts so that macropores on either side of a given microporous polymer strut are in communication through the given microporous polymer strut. In some embodiments, the macropores have a mean diameter in a range from about 0.5 to about 3.5 mm. In some embodiments, the macroporous polymer scaffold has a porosity of at least 50%. In some embodiments, the matrix capable of maintaining viability and function of a therapeutic cell population is selected from a group of matrices consisting of irradiated bone, decellularized bone, decellularized placenta stroma, decellularized thymus, and decellularized organs. In some embodiments, a source of matrices is selected from the group consisting of autologous, allogeneic, and xenogeneic. In some embodiments, the matrix capable of maintaining viability and function of a therapeutic cell population is made of a material in part or in whole selected from a group of materials consisting of glass, polystyrene, polypropylene, polyethylene, polyvinylidene fluoride, polyurethane, polyalginate, polysulphone, polyvinyl alcohol, acrylonitrile polymers, polyacrylamide, polycarbonate, polypentene, polypentane, nylon, magnetite, natural polysaccharide, modified polysaccharide, collagen, gelatin, and modified gelatin In some embodiments, the layer of material with selective permeability is manufactured using biocompatible materials allowing for free diffusion of particles small than 1 micrometer. In some embodiments, the layer of material with selective permeability is manufactured using biocompatible materials that do not allow for substantial immune recognition of said cells inside said material.

Some embodiments disclosed herein relate to a method of treating an inflammatory condition. In some embodiments, the method includes selecting a population of cells producing soluble anti-inflammatory mediators, culturing the cells producing soluble anti-inflammatory mediators with a matrix in vitro so as to allow adherence of said cells to said matrix, overlaying a material with selective permeability over said cells and said matrix so as to allow for diffusion of soluble factors through said material but not escape of cells, and implanting said enclosed matrix containing therapeutic cells into a patient in need. In some embodiments, the inflammatory condition is characterized by elevated levels of inflammatory mediators selected from the group consisting of IL-1, IL-2, IL-5, IL-6, IL-8, IL-12, IL-15, IL-17, IL-18, IL-21, IL-23, TNF-alpha, Interferon-gamma, and TRANCE. In some embodiments, the inflammatory condition is selected from the group consisting of autoimmunity, transplant rejection, and aging. In some embodiments, the population of cells producing soluble anti-inflammatory mediators are selected from the group consisting of immature dendritic cells, lymphoid dendritic cells, alternatively activated macrophages, bone marrow mononuclear cells, mesenchymal stem cells, T regulatory cells, NKT cells, hematopoietic stem cells, cord matrix mononuclear cells, adipose tissue mononuclear cells, placental matrix mononuclear cells, cord blood mononuclear cells, and CD5 positive B cells. In some embodiments, the cell populations are selected from the group of sources selected from autologous, allogeneic, and xenogeneic. In some embodiments, the cells are derived from one or a plurality of cell lines. In some embodiments, the enclosed matrix containing therapeutic cells is administered subcutaneously in a manner allowing for subsequent explantation.

Some embodiments disclosed herein relate to a method of modifying an antibody mediated immune response. In some embodiments, the method includes selecting a population of cells producing soluble immune modulators, culturing said cells producing soluble immune modulators with a matrix in vitro so as to allow adherence of said cells to said matrix, overlaying a material with selective permeability over said cells and said matrix so as to allow for diffusion of soluble factors through said material but not escape of cells, and implanting said enclosed matrix containing therapeutic cells into a patient in need. In some embodiments, an immune suppressant is administered prior to, and/or concurrent with, and/or subsequently to implantation of said enclosed matrix containing therapeutic cells. In some embodiments, the immune suppressant selectively inhibits B cell responses. In some embodiments, the immune suppressant selectively inhibits T cell responses. In some embodiments, the cell population producing soluble anti-inflammatory mediators is selected from a group of cells consisting of immature dendritic cells, lymphoid dendritic cells, alternatively activated macrophages, bone marrow mononuclear cells, mesenchymal stem cells, T regulatory cells, NKT cells, hematopoietic stem cells, cord matrix mononuclear cells, adipose tissue mononuclear cells, placental matrix mononuclear cells, cord blood mononuclear cells, and CD5 positive B cells. In some embodiments, the cell populations are selected from a group of sources selected from autologous, allogeneic, and xenogeneic. In some embodiments, the enclosed matrix containing therapeutic cells is administered subcutaneously in a manner allowing for subsequent explantation.

Some embodiments disclosed herein relate to a method of modifying an cell mediated immune response. In some embodiments, the method includes selecting a population of cells producing soluble immune modulators, culturing said cells producing soluble immune modulators with a matrix in vitro so as to allow adherence of said cells to said matrix, overlaying a material with selective permeability over said cells and said matrix so as to allow for diffusion of soluble factors through said material but not escape of cells, and implanting said enclosed matrix containing therapeutic cells into a patient in need. In some embodiments, an immune suppressant is administered prior to, and/or concurrent with, and/or subsequently to implantation of said enclosed matrix containing therapeutic cells. In some embodiments, the immune suppressant selectively inhibits B cell responses. In some embodiments, the immune suppressant selectively inhibits T cell responses. In some embodiments, the cell population producing soluble immune modulators is selected from a group of cells consisting of immature dendritic cells, lymphoid dendritic cells, alternatively activated macrophages, bone marrow mononuclear cells, mesenchymal stem cells, T regulatory cells, NKT cells, hematopoietic stem cells, cord matrix mononuclear cells, adipose tissue mononuclear cells, placental matrix mononuclear cells, cord blood mononuclear cells, and CD5 positive B cells. In some embodiments, the cell populations are selected from a group of sources selected from autologous, allogeneic, and xenogeneic. In some embodiments, the enclosed matrix containing therapeutic cells is administered subcutaneously in a manner allowing for subsequent explantation.

Some embodiments disclosed herein relate to a method of stimulating endogenous cellular repair processes. In some embodiments, the method includes selecting a population of cells producing soluble factors capable of augmenting endogenous cellular repair processes, culturing said cells producing soluble factors capable of augmenting endogenous cellular repair with a matrix in vitro so as to allow adherence of said cells to said matrix, overlaying a material with selective permeability over said cells and said matrix so as to allow for diffusion of soluble factors through said material but not escape of cells, and implanting said enclosed matrix containing therapeutic cells into a patient in need. In some embodiments, the cells producing soluble factors capable of augmenting endogenous cellular repair processes are manipulated to enhance production of said soluble factors capable of augmenting endogenous cellular repair factors. In some embodiments, the cells producing soluble factors capable of augmenting endogenous cellular repair are selected from a group of cells consisting of a differentiated cell expressing high growth factor production activity, a stem cell, and a cell or variety of cells expressing immune modulatory factors. In some embodiments, the stem cells are selected from the group consisting of embryonic stem cells, cord blood stem cells, placental stem cells, bone marrow stem cells, amniotic fluid stem cells, amniotic membrane stem cells, neuronal stem cells, circulating peripheral blood stem cells, mesenchymal stem cells, germinal stem cells, adipose tissue derived stem cells, exfoliated teeth derived stem cells, hair follicle stem cells, dermal stem cells, parthenogenically derived stem cells, reprogrammed stem cells, and side population stem cells. In some embodiments, the cell populations are selected from a group of sources selected from autologous, allogeneic, and xenogeneic. In some embodiments, the enclosed matrix containing therapeutic cells is administered subcutaneously in a manner allowing for subsequent explantation.

Some embodiments disclosed herein relate to a method of treating diabetes. In some embodiments, the method includes obtaining a population of cells capable of producing insulin in a glucose-inducible manner, obtaining a population of cells secreting trophic factors, said trophic factors promoting viability and function of said cells capable of producing insulin in a glucose-inducible manner, inserting the cells capable of producing insulin and cells secreting trophic factors into a porous matrix, and enclosing said porous matrix using a semipermeable material. In some embodiments, the cells capable of producing insulin are selected from the group consisting of differentiated stem cells along the pancreatic lineage, cells transfected with an glucose-inducible insulin promoter, pancreatic islet cells, pancreatic progenitor cells, ductal pancreatic progenitor cells, and xenogeneic islet cells. In some embodiments, the population of cells secreting trophic factors are selected from the group consisting of embryonic stem cells, cord blood stem cells, placental stem cells, bone marrow stem cells, amniotic fluid stem cells, amniotic membrane stem cells, neuronal stem cells, circulating peripheral blood stem cells, mesenchymal stem cells, germinal stem cells, adipose tissue derived stem cells, exfoliated teeth derived stem cells, sertoli cells, hair follicle stem cells, dermal stem cells, parthenogenically derived stem cells, reprogrammed stem cells, and side population stem cells. In some embodiments, the porous matrix is a macroporous polymer scaffold including porous walls that are essentially non-membranous. In some embodiments, the porous walls include microporous polymer struts defining macropores which are interconnected by macroporous passageways. In some embodiments, the microporous polymer struts contain microporous passageways extending through said microporous polymer struts so that macropores on either side of a given microporous polymer strut are in communication through said given microporous polymer strut. In some embodiments, the macropores have a mean diameter in a range from about 0.5 to about 3.5 mm. In some embodiments, the macroporous polymer scaffold has a porosity of at least 50%. In some embodiments, the porous matrix is selected from a group of matrices consisting of irradiated bone, decellularized bone, decellularized placenta stroma, decellularized thymus, and decellularized organs. In some embodiments, the semipermeable material does not allow exit of cells. In some embodiments, the cells are collected from a source selected from a group of sources consisting of autologous, allogeneic, and xenogeneic.

Some embodiments disclosed herein relate to a method of accelerating hematopoietic recovery subsequent to an insult to the hematopoietic system. In some embodiments, the method includes selecting a population of cells producing soluble factors capable of augmenting hematopoietic recovery, culturing said cells producing soluble factors capable of augmenting hematopoietic recovery with a matrix in vitro so as to allow adherence of said cells to said matrix, overlaying a material with selective permeability over said cells and said matrix so as to allow for diffusion of soluble factors through said material but not escape of cells, and implanting said enclosed matrix containing therapeutic cells into a patient in need. In some embodiments, the population of cells producing factors capable of augmenting hematopoietic recovery are selected from a group of cells consisting of embryonic stem cells, cord blood stem cells, placental stem cells, bone marrow stem cells, amniotic fluid stem cells, amniotic membrane stem cells, neuronal stem cells, circulating peripheral blood stem cells, mesenchymal stem cells, germinal stem cells, adipose tissue derived stem cells, exfoliated teeth derived stem cells, sertoli cells, hair follicle stem cells, dermal stem cells, parthenogenically derived stem cells, reprogrammed stem cells and side population stem cells. In some embodiments, the matrix is a macroporous polymer scaffold includes porous walls that are essentially non-membranous. In some embodiments, the porous walls include microporous polymer struts defining macropores which are interconnected by macroporous passageways. In some embodiments, the microporous polymer struts containing microporous passageways extending through said microporous polymer struts so that macropores on either side of a given microporous polymer strut are in communication through said given microporous polymer strut. In some embodiments, the macropores have a mean diameter in a range from about 0.5 to about 3.5 mm. In some embodiments, the macroporous polymer scaffold has a porosity of at least 50%. In some embodiments, the matrix is selected from a group of matrices consisting of irradiated bone, decellularized bone, decellularized placenta stroma, decellularized thymus, and decellularized organs. In some embodiments, the cells are derived from sources selected from a group of sources consisting of allogeneic, autologous, and xenogeneic. In some embodiments, a dose or plurality of doses of a factor capable of augmenting hematopoietic recovery is also administered. In some embodiments, the factor capable of augmenting hematopoietic recovery is selected from the group consisting of G-CSF, GM-CSF, human chorionic gonadotropin, an inhibitor of GSK-3beta, a histone deacetylase inhibitor, a DNA methyltransferase inhibitor, a hyaluronic acid fragment, IL-1, IL-3, IL-7, thrombopoietin, and parathyroid hormone.

In some embodiments, a permeable material as disclosed herein is not used so as to allow implanted cells to migrate out of said matrix.

In some embodiments, the therapeutic cell population is derived from donor cells in the context of a solid organ transplant. In some embodiments, the therapeutic cell population is derived from recipient cells in the context of a hematopoietic stem cell transplant where prevention of donor reactivity to recipient tissue is desired. In some embodiments, the therapeutic cell population is a cell population possessing ability to induce apoptosis or inactivation of cells that are self-reactive. In some embodiments, the self-reactive cells are lymphocytes recognizing recipient tissue in the context of a hematopoietic stem cell transplant. In some embodiments, the self-reactive cells are lymphocytes recognizing donor tissue in the context of a solid organ transplant.

Some embodiments disclosed herein relate to an implantable device including a therapeutic cell population, a matrix capable of maintaining viability and function of said therapeutic cell population, and a layer of material with selective permeability surrounding said matrix capable of maintaining viability and function of said therapeutic cell population. In some embodiments, the therapeutic cell population is derived from the steps of extracting an adult tissue, dedifferentiating the adult tissue to convey lineage plasticity, and differentiating said adult tissue into thymic medullary epithelial cells or progenitors thereof. In some embodiments, the adult tissue is skin. In some embodiments, the adult tissue possesses lineage plasticity. In some embodiments, the adult tissue possessing lineage plasticity is a stem cell. In some embodiments, the stem cell is selected from a group of cells consisting of embryonic stem cells, inducible pluripotent stem cells, nuclear transfer derived stem cells, cord blood stem cells, placental stem cells, bone marrow stem cells, amniotic fluid stem cells, neuronal stem cells, circulating peripheral blood stem cells, mesenchymal stem cells, germinal stem cells, adipose tissue derived stem cells, exfoliated teeth derived stem cells, hair follicle stem cells, dermal stem cells, parthenogenically derived stem cells, reprogrammed stem cells and side population stem cells. In some embodiments, the embryonic stem cells are totipotent and express one or more antigens selected from the group consisting of stage-specific embryonic antigens (SSEA) 3, SSEA 4, Tra-1-60 and Tra-1-81, Oct-3/4, Cripto, gastrin-releasing peptide (GRP) receptor, podocalyxin-like protein (PODXL), Rex-1, GCTM-2, Nanog, and human telomerase reverse transcriptase (hTERT). In some embodiments, the cord blood stem cells are multipotent and capable of differentiating into endothelial, smooth muscle, and neuronal cells. In some embodiments, the cord blood stem cells are identified based on expression of one or more antigens selected from the group consisting of SSEA-3, SSEA-4, CD9, CD34, c-kit, OCT-4, Nanog, and CXCR-4. In some embodiments, the cord blood stem cells do not express one or more markers selected from the group consisting of CD3, CD34, CD45, and CD1 1b. In some embodiments, the placental stem cells are isolated from the placental structure. In some embodiments, the placental stem cells are identified based on expression of one or more antigens selected from the group consisting of Oct-4, Rex-1, CD9, CD13, CD29, CD44, CD166, CD90, CD105, SH-3, SH-4, TRA-1-60, TRA-1-81, SSEA-4 and Sox-2. In some embodiments, the bone marrow stem cells include bone marrow mononuclear cells. In some embodiments, the bone marrow stem cells are selected based on the ability to differentiate into one or more of endothelial cells, smooth muscle cells, and neuronal cells. In some embodiments, the bone marrow stem cells are selected based on expression of one or more of CD34, c-kit, flk-1, Stro-1, CD105, CD73, CD31, CD146, vascular endothelial-cadherin, CD133 and CXCR-4. In some embodiments, the placental stem cells are isolated from the Wharton's Jelly. In some embodiments, the placental stem cells are mesenchymal in morphology. In some embodiments, the placental cell expresses one or more cytokines associated with a regenerative activities. In some embodiments, the cells with lineage plasticity are differentiated into thymic medullary epithelial cells by culture in media lacking leukemia inhibitory factor and exposure to human fibroblast growth factor 7, human fibroblast growth factor 10, human bone morphogenetic protein 4, and human epithelial growth factor. In some embodiments, the concentration of human fibroblast growth factor 7 is 20 ng/mL. In some embodiments, the concentration of human fibroblast growth factor 10 is 20 ng/mL. In some embodiments, the concentration of human bone morphogenetic protein 4 is 20 ng/mL. In some embodiments, the concentration of human epithelial growth factor is 50 ng/mL.

Some embodiments disclosed herein relate to a method of inducing allograft tolerance. In some embodiments, the method includes extraction of donor mesenchymal stem cells, culturing said donor mesenchymal stem cells under conditions capable of inducing dedifferentiation, differentiating said donor dedifferentiated mesenchymal stem cells into cells expressing properties shared with thymic medullary epithelial cells, and administering said differentiated donor mesenchymal stem cells possessing properties shared with thymic medullary epithelial cells into a recipient prior to allograft transplantation. In some embodiments, the donor mesenchymal stem cells are derived from tissue selected from the group consisting of circulating blood, testis, fallopian tube, bone marrow, cord blood, hair follicle, menstrual blood, Wharton's Jelly, and adipose tissue. In some embodiments, the donor mesenchymal stem cells are dedifferentiated by processes selected from the group consisting of somatic cell nuclear transfer, cytoplasmic transfer, treatment with epigenetic acting agents, treatment with factors known to cause formation of inducible pluripotent stem cells, and treatment with acidic conditions. In some embodiments, the somatic cell nuclear transfer is performed by introducing nucleus of said donor mesenchymal stem cell into an enucleated recipient oocyte. In some embodiments, a process is performed to induce activation of said enucleated recipient oocyte. In some embodiments, pluripotent stem cells are derived from said activated recipient oocyte. In some embodiments, the pluripotent stem cells possess ability to self-renew for more than one year. In some embodiments, the pluripotent stem cells possess expression of hTERT. In some embodiments, inhibition of spontaneous differentiation of said pluripotent stem cells is achieved by growth in media conditioned by feeder cells. In some embodiments, the inhibition of spontaneous differentiation of said pluripotent stem cells is achieved by growth on a feeder layer. In some embodiments, the feeder cells are fibroblasts. In some embodiments, the cytoplasmic transfer is performed using cytoplasm from a pluripotent stem cell into a mesenchymal stem cell derived from a donor of an allograft In some embodiments, the pluripotent stem cell is selected from the group consisting of embryonic stem cells, parthenogenic stem cells, somatic cell nuclear transfer generated stem cells, and inducible pluripotent stem cells. In some embodiments, the cytoplasmic transfer is induced by permeabilization of said mesenchymal stem cell membrane utilizing an agent that induces pore formation in said membrane. In some embodiments, the agent capable of inducing pore formation in said membrane is streptolysin O. In some embodiments, induction of membrane permeability is performed using electrical current. In some embodiments, the epigenetic acting agents are DNA methyltransferase inhibitors. In some embodiments, the epigenetic acting agents are histone deacetylase inhibitors. In some embodiments, the DNA methyltransferase inhibitor is 5-azacytidine. In some embodiments, the histone deacetylase inhibitor is selected from the group consisting of valproic acid, trichostatin A, and sodium phenylbutyrate. In some embodiments, the induced pluripotent stem cell is generated by introduction of genes selected from the group consisting of SOX-2, Oct4, c-Myc, Klf4, nanog, LIN28, and Glis1.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the claims.

REFERENCES, EACH OF WHICH IS HEREBY INCORPORATED BY REFERENCE IN ITS ENTIRETY

1. Orlic, D., et al., *Bone marrow cells regenerate infarcted myocardium.* Nature, 2001. 410(6829): p. 701-5.
2. Hamano, K., et al., *Local implantation of autologous bone marrow cells for therapeutic angiogenesis in patients with ischemic heart disease: clinical trial and preliminary results.* Jpn Circ J, 2001. 65(9): p. 845-7.
3. Stamm, C., et al., *Autologous bone-marrow stem-cell transplantation for myocardial regeneration.* Lancet, 2003. 361(9351): p. 45-6.
4. Kondziolka, D., et al., *Neurotransplantation for patients with subcortical motor stroke: a phase 2 randomized trial.* J Neurosurg, 2005. 103(1): p. 38-45.
5. Kordella, T., *The Edmonton Protocol. The future of islet transplantation?* Diabetes Forecast, 2003. 56(2): p. 58-62.
6. Shapiro, A. M., et al., *International trial of the Edmonton protocol for islet transplantation.* N Engl J Med, 2006. 355(13): p. 1318-30.

7. Bang, O. Y., et al., *Autologous mesenchymal stem cell transplantation in stroke patients*. Ann Neurol, 2005. 57(6): p. 874-82.
8. Mohamadnejad, M., et al., *Phase 1 human trial of autologous bone marrow-hematopoietic stem cell transplantation in patients with decompensated cirrhosis*. World J Gastroenterol, 2007. 13(24): p. 3359-63.
9. Wang, X. X., et al., *Transplantation of autologous endothelial progenitor cells may be beneficial in patients with idiopathic pulmonary arterial hypertension: a pilot randomized controlled trial*. J Am Coll Cardiol, 2007. 49(14): p. 1566-71.
10. Nizankowski, R., et al., *The treatment of advanced chronic lower limb ischaemia with marrow stem cell autotransplantation*. Kardiol Pol, 2005. 63(4): p. 351-60; discussion 361.
11. Kim, S. Y., et al., *Siberian Sturgeon Oocyte Extract Induces Epigenetic Modifications of Porcine Somatic Cells and Improves Developmental Competence of SCNT Embryos*. Asian-Australas J Anim Sci, 2014. 27(2): p. 266-77.
12. Wen, D., et al., *Histone variant H3.3 is an essential maternal factor for oocyte reprogramming*. Proc Natl Acad Sci USA, 2014. 111(20): p. 7325-30.
13. Preskey, D., et al., *Synthetically modified mRNA for efficient and fast human iPS cell generation and direct transdifferentiation to myoblasts*. Biochem Biophys Res Commun, 2015.
14. Mesquita, F. C., et al., *Generation of human iPS cell line ihFib3.2 from dermal fibroblasts*. Stem Cell Res, 2015. 15(3): p. 445-448.
15. Hamalainen, R. H. and A. Suomalainen, *Generation and Characterization of Induced Pluripotent Stem Cells from Patients with mtDNA Mutations*. Methods Mol Biol, 2016. 1353: p. 65-75.
16. Thery, C., M. Ostrowski, and E. Segura, *Membrane vesicles as conveyors of immune responses*. Nature reviews. Immunology, 2009. 9(8): p. 581-93.
17. Ludwig, A. K. and B. Giebel, *Exosomes: Small vesicles participating in intercellular communication*. The international journal of biochemistry & cell biology, 2011.
18. Alvarez-Erviti, L., et al., *Lysosomal dysfunction increases exosome-mediated alpha-synuclein release and transmission*. Neurobiology of disease, 2011. 42(3): p. 360-7.
19. Silverman, J. M. and N. E. Reiner, *Exosomes and other microvesicles in infection biology: organelles with unanticipated phenotypes*. Cellular microbiology, 2011. 13(1): p. 1-9.
20. Pan, B. T. and R. M. Johnstone, *Fate of the transferrin receptor during maturation of sheep reticulocytes in vitro: selective externalization of the receptor*. Cell, 1983. 33(3): p. 967-78.
21. Alonso, R., et al., *Diacylglycerol kinase alpha regulates the formation and polarisation of mature multivesicular bodies involved in the secretion of Fas ligand-containing exosomes in T lymphocytes*. Cell death and differentiation, 2011. 18(7): p. 1161-73.
22. Zhang, H., et al., *CD4(+) T cell-released exosomes inhibit CD8(+) cytotoxic T-lymphocyte responses and antitumor immunity*. Cellular & molecular immunology, 2011. 8(1): p. 23-30.
23. Mathews, J. A., et al., *CD23 Sheddase A disintegrin and metalloproteinase 10 (ADAM10) is also required for CD23 sorting into B cell-derived exosomes*. The Journal of biological chemistry, 2010. 285(48): p. 37531-41.
24. Buschow, S. I., et al., *MHC class II-associated proteins in B-cell exosomes and potential functional implications for exosome biogenesis*. Immunology and cell biology, 2010. 88(8): p. 851-6.
25. Hwang, I. and D. Ki, *Receptor-mediated T cell absorption of antigen presenting cell-derived molecules*. Frontiers in bioscience: a journal and virtual library, 2011. 16: p. 411-21.
26. Viaud, S., et al., *Updated technology to produce highly immunogenic dendritic cell-derived exosomes of clinical grade: a critical role of interferon-gamma*. Journal of immunotherapy, 2011. 34(1): p. 65-75.
27. Clayton, A., et al., *Cancer exosomes express CD39 and CD73, which suppress T cells through adenosine production*. Journal of immunology, 2011. 187(2): p. 676-83.
28. Battke, C., et al., *Tumour exosomes inhibit binding of tumour-reactive antibodies to tumour cells and reduce ADCC*. Cancer immunology, immunotherapy: CII, 2011. 60(5): p. 639-48.
29. Lachenal, G., et al., *Release of exosomes from differentiated neurons and its regulation by synaptic glutamatergic activity*. Molecular and cellular neurosciences, 2011. 46(2): p. 409-18.
30. Faure, J., et al., *Exosomes are released by cultured cortical neurones*. Molecular and cellular neurosciences, 2006. 31(4): p. 642-8.
31. Fitzner, D., et al., *Selective transfer of exosomes from oligodendrocytes to microglia by macropinocytosis*. Journal of cell science, 2011. 124(Pt 3): p. 447-58.
32. Mincheva-Nilsson, L. and V. Baranov, *The role of placental exosomes in reproduction*. American journal of reproductive immunology, 2010. 63(6): p. 520-33.
33. Mincheva-Nilsson, L., et al., *Placenta-derived soluble MHC class I chain-related molecules down-regulate NKG2D receptor on peripheral blood mononuclear cells during human pregnancy: a possible novel immune escape mechanism for fetal survival*. Journal of immunology, 2006. 176(6): p. 3585-92.
34. Murphy, M. P., et al., *Allogeneic endometrial regenerative cells: an "Off the shelf solution" for critical limb ischemia?* Journal of translational medicine, 2008. 6: p. 45.
35. Raposo, G., et al., *B lymphocytes secrete antigen-presenting vesicles*. The Journal of experimental medicine, 1996. 183(3): p. 1161-72.
36. Abusamra, A. J., et al., *Tumor exosomes expressing Fas ligand mediate CD8+T-cell apoptosis*. Blood cells, molecules & diseases, 2005. 35(2): p. 169-73.
37. Ichim, T. E., R. Zhong, and W. P. Min, *Prevention of allograft rejection by in vitro generated tolerogenic dendritic cells*. Transplant immunology, 2003. 11(3-4): p. 295-306.
38. Popov, I., et al., *Preventing autoimmune arthritis using antigen-specific immature dendritic cells: a novel tolerogenic vaccine*. Arthritis research & therapy, 2006. 8(5): p. R141.
39. Luketic, L., et al., *Antigen presentation by exosomes released from peptide-pulsed dendritic cells is not suppressed by the presence of active CTL*. Journal of immunology, 2007. 179(8): p. 5024-32.
40. Segura, E., S. Amigorena, and C. Thery, *Mature dendritic cells secrete exosomes with strong ability to induce antigen-specific effector immune responses*. Blood cells, molecules & diseases, 2005. 35(2): p. 89-93.
41. Ruffner, M. A., et al., *B7-1/2, but not PD-L1/2 molecules, are required on IL-10-treated tolerogenic DC and 41. *DC-derived exosomes for in vivo function.* European journal of immunology, 2009. 39(11): p. 3084-90.
42. Yang, X., et al., *Exosomes derived from immature bone marrow dendritic cells induce tolerogenicity of intestinal transplantation in rats.* The Journal of surgical research, 2011. 171(2): p. 826-32.
43. Peche, H., et al., *Induction of tolerance by exosomes and short-term immunosuppression in a fully MHC-mismatched rat cardiac allograft model.* American journal of transplantation: official journal of the American Society of Transplantation and the American Society of Transplant Surgeons, 2006. 6(7): p. 1541-50.
44. Kim, S. H., et al., *MHC class II+ exosomes in plasma suppress inflammation in an antigen-specific and Fas ligand/Fas-dependent manner.* Journal of immunology, 2007. 179(4): p. 2235-41.
45. Marleau, A. M., et al., *Chimerism of murine fetal bone marrow by maternal cells occurs in late gestation and persists into adulthood.* Laboratory investigation; a journal of technical methods and pathology, 2003. 83(5): p. 673-81.
46. Kara, R. J., et al., *Fetal Cells Traffic to Injured Maternal Myocardium and Undergo Cardiac Differentiation.* Circulation research, 2011.
47. Khashan, A. S., et al., *Pregnancy and the risk of autoimmune disease.* PloS one, 2011. 6(5): p. e19658.
48. Ernerudh, J., G. Berg, and J. Mjosberg, *Regulatory T helper cells in pregnancy and their roles in systemic versus local immune tolerance.* American journal of reproductive immunology, 2011. 66 Suppl 1: p. 31-43.
49. Lin, Q. D. and L. H. Qiu, *Pathogenesis, diagnosis, and treatment of recurrent spontaneous abortion with immune type.* Frontiers of medicine in China, 2010. 4(3): p. 275-9.
50. Pandey, M. K., R. Rani, and S. Agrawal, *An update in recurrent spontaneous abortion.* Archives of gynecology and obstetrics, 2005. 272(2): p. 95-108.
51. Frangsmyr, L., et al., *Cytoplasmic microvesicular form of Fas ligand in human early placenta: switching the tissue immune privilege hypothesis from cellular to vesicular level.* Molecular human reproduction, 2005. 11(1): p. 35-41.
52. Taylor, D. D., S. Akyol, and C. Gercel-Taylor, *Pregnancy-associated exosomes and their modulation of T cell signaling.* Journal of immunology, 2006. 176(3): p. 1534-42.
53. Sabapatha, A., C. Gercel-Taylor, and D. D. Taylor, *Specific isolation of placenta-derived exosomes from the circulation of pregnant women and their immunoregulatory consequences.* American journal of reproductive immunology, 2006. 56(5-6): p. 345-55.
54. Hedlund, M., et al., *Human placenta expresses and secretes NKG2D ligands via exosomes that down-modulate the cognate receptor expression: evidence for immunosuppressive function.* Journal of immunology, 2009. 183(1): p. 340-51.
55. Forger, F., et al., *Pregnancy induces numerical and functional changes of CD4+CD25 high regulatory T cells in patients with rheumatoid arthritis.* Annals of the rheumatic diseases, 2008. 67(7): p. 984-90.
56. Airas, L., et al., *Immunoregulatory factors in multiple sclerosis patients during and after pregnancy: relevance of natural killer cells.* Clinical and experimental immunology, 2008. 151(2): p. 235-43.
57. Gatson, N. N., et al., *Induction of pregnancy during established EAE halts progression of CNS autoimmune injury via pregnancy-specific serum factors.* Journal of neuroimmunology, 2011. 230(1-2): p. 105-13.
58. Taylor, D. D. and C. Gercel-Taylor, *Tumour-derived exosomes and their role in cancer-associated T-cell signalling defects.* British journal of cancer, 2005. 92(2): p. 305-11.
59. Valenti, R., et al., *Tumor-released microvesicles as vehicles of immunosuppression.* Cancer research, 2007. 67(7): p. 2912-5.
60. Greten, T. F., M. P. Manns, and F. Korangy, *Myeloid derived suppressor cells in human diseases.* International immunopharmacology, 2011. 11(7): p. 802-7.
61. Szajnik, M., et al., *Tumor-derived microvesicles induce, expand and up-regulate biological activities of human regulatory T cells (Treg).* PloS one, 2010. 5(7): p. e11469.
62. Weiner, H. L., et al., *Oral tolerance.* Immunological reviews, 2011. 241(1): p. 241-59.
63. Wei, W., et al., *A multicenter, double-blind, randomized, controlled phase III clinical trial of chicken type II collagen in rheumatoid arthritis.* Arthritis research & therapy, 2009. 11(6): p. R180.
64. Benson, J. M., et al., *Oral administration of myelin basic protein is superior to myelin in suppressing established relapsing experimental autoimmune encephalomyelitis.* Journal of immunology, 1999. 162(10): p. 6247-54.
65. Hafler, D. A., et al., *Oral administration of myelin induces antigen-specific TGF-beta 1 secreting T cells in patients with multiple sclerosis.* Annals of the New York Academy of Sciences, 1997. 835: p. 120-31.
66. Ostman, S., M. Taube, and E. Telemo, *Tolerosome-induced oral tolerance is MHC dependent.* Immunology, 2005. 116(4): p. 464-76.
67. Almqvist, N., et al., *Serum-derived exosomes from antigen-fed mice prevent allergic sensitization in a model of allergic asthma.* Immunology, 2008. 125(1): p. 21-7.
68. Meng, X., et al., *Endometrial regenerative cells: a novel stem cell population.* Journal of translational medicine, 2007. 5: p. 57.
69. Ichim, T. E., et al., *Placental mesenchymal and cord blood stem cell therapy for dilated cardiomyopathy.* Reproductive biomedicine online, 2008. 16(6): p. 898-905.
70. Ichim, T. E., et al., *Feasibility of combination allogeneic stem cell therapy for spinal cord injury: a case report.* International archives of medicine, 2010. 3: p. 30.
71. Yang, W. Z., et al., *Human umbilical cord blood-derived mononuclear cell transplantation: case series of 30 subjects with hereditary ataxia.* Journal of translational medicine, 2011. 9: p. 65.

What is claimed is:

1. An implantable device, comprising:
a therapeutic cell population comprising thymic medullary epithelial cells;
a decellularized placental matrix capable of maintaining viability and function of said therapeutic cell population; and
a biocompatible material with selective permeability allowing free exchange of molecules without cell escape overlaying said matrix capable of maintaining viability and function of said therapeutic cell population.

2. The implantable device of claim 1, wherein said therapeutic cell population comprises differentiated cells expressing high growth factor production activity or cells expressing immune modulatory.

3. The implantable device of claim 2, wherein said differentiated cells produce high levels of growth factors by ex vivo manipulation or naturally express high levels of growth factors.

4. The implantable device of claim 1, wherein said therapeutic cell population comprises donor cells or recipient cells.

5. The implantable device of claim 1, wherein said matrix further comprises a macroporous polymer scaffold comprising non-membranous porous walls, said non-membranous porous walls comprising microporous polymer struts defining macropores which are interconnected by macroporous passageways, said microporous polymer struts comprising microporous passageways extending through said microporous polymer struts so that macropores on either side of a given microporous polymer strut are in communication through said given microporous polymer strut, said macropores having a mean diameter in a range from about 0.5 to about 3.5 mm, and said macroporous polymer scaffold having a porosity of at least 50%.

6. The implantable device of claim 1, wherein said matrix further comprises a material selected from the group consisting of irradiated bone, decellularized bone, decellularized placenta stroma, decellularized thymus, and decellularized organs.

7. The implantable device of claim 1, wherein said matrix further comprises a material selected from a group consisting of glass, polystyrene, polypropylene, polyethylene, polyvinylidene fluoride, polyurethane, polyalginate, polysulphone, polyvinyl alcohol, acrylonitrile polymers, polyacrylamide, polycarbonate, polypentene, polypentane, nylon, magnetite, natural polysaccharide, modified polysaccharide, collagen, gelatin, and modified gelatin.

8. The implantable device of claim 1, wherein said biocompatible material with selective permeability is manufactured using biocompatible materials allowing for free diffusion of particles smaller than 1 micrometer.

9. The implantable device of claim 1, wherein said biocompatible material with selective permeability is manufactured using biocompatible materials that do not allow for substantial immune recognition of said cells inside said material.

10. The implantable device of claim 1, wherein said thymic medullary epithelial cells are donor derived.

11. The implantable device of claim 1, wherein said matrix provides an environment for the therapeutic cell population to survive.

12. The implantable device of claim 1, wherein said decellularized placental matrix is contacted with fibronectin and a glycosaminoglycan.

13. The implantable device of claim 1, wherein said therapeutic cell population is adherent to said matrix, and wherein said matrix is enclosed within said biocompatible material.

14. The implantable device of claim 1, wherein said biocompatible material comprises pores of sufficient size to prevent passage of the therapeutic cell population.

15. The implantable device of claim 1, wherein said therapeutic cell population further comprises immature dendritic cells, lymphoid dendritic cells, alternatively activated macrophages, bone marrow mononuclear cells, mesenchymal stem cells, T regulatory cells, NKT cells, hematopoietic stem cells, cord matrix mononuclear cells, adipose tissue mononuclear cells, placental matrix mononuclear cells, cord blood mononuclear cells, or CD5 positive B cells.

* * * * *